(12) United States Patent
Brown

(10) Patent No.: US 12,178,514 B2
(45) Date of Patent: Dec. 31, 2024

(54) VOLUMETRIC IMAGING

(71) Applicant: Boston Scientific, Scimed Inc., Maple Grove, MN (US)

(72) Inventor: Andrew E. Brown, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 922 days.

(21) Appl. No.: 16/283,354

(22) Filed: Feb. 22, 2019

(65) Prior Publication Data

US 2019/0262076 A1 Aug. 29, 2019

Related U.S. Application Data

(63) Continuation of application No. PCT/IB2019/051198, filed on Feb. 14, 2019.

(Continued)

(51) Int. Cl.
*A61B 34/10* (2016.01)
*A61B 18/02* (2006.01)
(Continued)

(52) U.S. Cl.
CPC .............. *A61B 34/10* (2016.02); *A61B 18/02* (2013.01); *A61B 18/1492* (2013.01);
(Continued)

(58) Field of Classification Search
CPC ......... A61B 34/10; A61B 34/20; A61B 90/11; A61B 90/36; A61B 18/02; A61B 18/1492;
(Continued)

(56) References Cited

U.S. PATENT DOCUMENTS

2002/0040220 A1 4/2002 Zvuloni et al.
2007/0055131 A1* 3/2007 Deinzer ................. A61B 5/416
600/407

(Continued)

OTHER PUBLICATIONS

International Search Report and Written Opinion received for PCT Patent Application No. PCT/IB2019/051198, mailed on Jun. 30, 2019, 13 pages.

(Continued)

*Primary Examiner* — Michael F Peffley
*Assistant Examiner* — Bo Ouyang
(74) *Attorney, Agent, or Firm* — Pauly, DeVries Smith & Deffner LLC

(57) ABSTRACT

Aspects of the disclosure include systems and methods for planning and/or performing an ablation procedure. Volumetric image data including a needle, such as a physical ablation needle or a virtual needle, can be analyzed to segment the needle within the volume. A first cross-sectional, two-dimensional view of the volume showing a first plane in which an axis defined by the needle lies can be generated and displayed. The view can be manipulated to display a generated second cross-sectional, two-dimensional view of the volume showing a second plane through the volume in which the longitudinal axis defined by the virtual needle lies, wherein the second plane is different from the first plane. Additional segmented features such as lesions in the image data, treatment regions, isotherms, and the like can be included in views to be analyzed from a plurality of views that include the needle.

28 Claims, 22 Drawing Sheets

Related U.S. Application Data

(60) Provisional application No. 62/634,581, filed on Feb. 23, 2018.

(51) Int. Cl.
  *A61B 18/14* (2006.01)
  *A61B 90/00* (2016.01)
  *A61B 90/11* (2016.01)
  *A61B 8/08* (2006.01)
  *A61B 17/00* (2006.01)
  *A61B 18/00* (2006.01)
  *A61B 34/20* (2016.01)

(52) U.S. Cl.
  CPC .............. *A61B 90/11* (2016.02); *A61B 90/36* (2016.02); *A61B 8/483* (2013.01); *A61B 2017/00092* (2013.01); *A61B 2018/00101* (2013.01); *A61B 2018/00577* (2013.01); *A61B 2018/0262* (2013.01); *A61B 2018/0293* (2013.01); *A61B 2034/107* (2016.02); *A61B 34/20* (2016.02); *A61B 2090/364* (2016.02)

(58) Field of Classification Search
  CPC .............. A61B 8/483; A61B 2034/107; A61B 2018/00101; A61B 2018/00577; A61B 2018/0262; A61B 2018/0293
  See application file for complete search history.

(56) References Cited

U.S. PATENT DOCUMENTS

| | | | |
|---|---|---|---|
| 2011/0137156 A1* | 6/2011 | Razzaque | A61B 34/20 600/424 |
| 2011/0191082 A1 | 8/2011 | Blezek et al. | |
| 2012/0089008 A1* | 4/2012 | Strehl | G01R 33/286 600/411 |
| 2013/0197357 A1* | 8/2013 | Green | A61B 34/10 600/424 |
| 2016/0117857 A1* | 4/2016 | State | A61B 34/20 345/420 |
| 2017/0224426 A1 | 8/2017 | Lavallee | |

OTHER PUBLICATIONS

"First Office Action," for Chinese Patent Application No. 201980028134.5 mailed Sep. 1, 2023 (12 pages) with English translation.

* cited by examiner

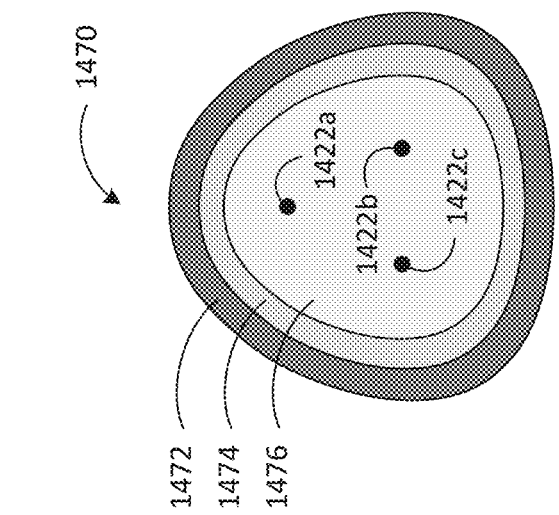
FIG. 14C
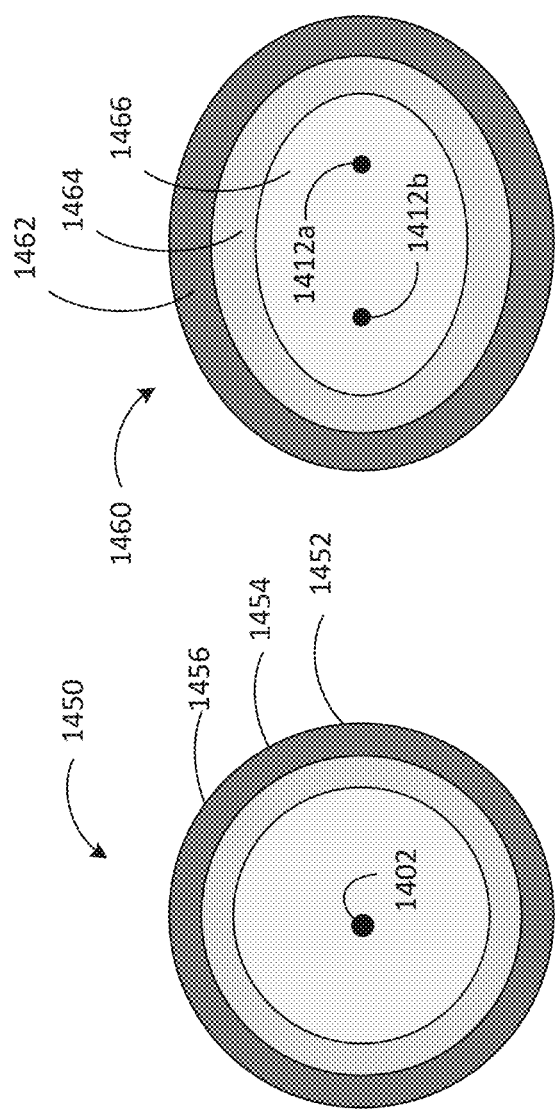
FIG. 14B
FIG. 14A

VOLUMETRIC IMAGING

CROSS REFERENCE TO RELATED APPLICATION

This application claims the benefit of U.S. Provisional Application No. 62/634,581, filed Feb. 23, 2018. This application claims the benefit PCT/IB2019/051198, filed Feb. 14, 2019, which claims priority to U.S. Provisional Application No. 62/634,581, filed Feb. 23, 2018. These applications are incorporated herein by reference in their entirety.

BACKGROUND

A variety of surgical ablation modalities are available. These include, inter alia, cryoabaltion, microwave ablation, radiofrequency ablation and electroporation modalities, for example.

In cryoablation, a cryoprobe or cryoneedle, is placed in or near a tissue to be ablated, the temperature of the probe tip is lowered to cryogenic temperatures in order to freeze the target tissue. One or more cycles of freezing and thawing of the tissue results in ablation of the tissue.

Cryosurgical systems comprise one or more cryoprobe connected to one or more cryofluid sources. Such systems are described in the commonly-assigned U.S. Pat. No. 8,066,697 and in published application, U.S. Pub. No. 2010/0256620 A1, the disclosure of which is hereby incorporated by reference in its entirety. In such cryosurgical systems, a cryofluid can be delivered from a cryofluid source to one or more cryoprobes. The cryoprobe can be cooled as a result of expansion of the cryofluid, thereby freezing tissue in the vicinity of a tip of the cryoprobe. Some such systems include an electrical heater (in the form of a high resistance wire) positioned within the probe shaft of each cryoprobe to thaw tissue after freezing to facilitate removal of the cryoprobe.

Microwave ablation systems typically include a microwave probe having a microwave antenna, typically close to the probe tip. Energy delivered to the antenna is used to heat tissue to cause ablation. Such systems typically include a microwave energy generator and one or more microwave needles or probes, with which to carry out the ablation.

In radiofrequency ablation (RFA), tissue is ablated using the heat generated from alternating current passing through tissue between two electrodes. At least one of these electrodes is typically carried on a needle or other probe that is placed in or close to the tissue to be ablated; the tissue around the needle is ablated by the heat generated.

In electroporation ablation modalities, probes are placed in or around a target tissue and a pulsed electric fields are generated between probes. This permiablises cell membranes leading to cell death.

Percutaneous as well as catheter based approaches are available, and the technique has been used widely to ablate inter alia, tumorous tissue in the treatment of cancer, heart tissue for the control of arrhythmias and nerve tissue for the control of pain among many others.

Volumetric imaging of patient tissue, for example, of CT scans, is performed as a plurality of parallel cross-sectional slices. Typically, during visualization of the scans for treatment planning and analysis, a few slices of interest are observed proximate a region of interest (e.g., a patient lesion). Such slices can be viewed, for example, to assist a clinician from inserting a treatment apparatus into the patient and/or to view the effects of the treatment.

However, as the slices generally represent parallel planes, objects in the images that intersect the planes at an angle, such as a treatment needle inserted into the tissue at an angle relative to the planes, can be difficult to observe. For example, a portion of a needle may be observable in a cross-sectional slice, however, it can be difficult to determine the orientation of the needle (e.g., whether it is angled upward or downward relative to the plane). Similarly, it can be difficult to analyze and interpret the location of the treatment device and/or treated region while relying on parallel planes of images that may not be conveniently oriented.

SUMMARY

Aspects of the disclosure are generally directed toward systems and methods for planning and/or performing a procedure, such as an ablation procedure. Typically such procedures involve the use of at least one ablation probe or needle. In some examples, methods can include receiving volumetric image data representing a volume of patient tissue, wherein the volumetric image data is constructed from a series of two-dimensional images of the patient tissue, and includes a virtual needle. The virtual needle can be positioned, for example, by a system user.

The method can include segmenting the virtual needle within the volumetric image data such that the virtual needle defines a longitudinal axis extending through the volume and generating a first cross-sectional, two-dimensional view of the volume, the first cross-sectional, two-dimensional view showing a first plane through the volume in which the axis defined by the virtual needle lies. The first cross-sectional, two-dimensional view can be presented on a display. Similarly, the method can include generating and displaying a second cross-sectional, two-dimensional view of the volume, the second cross-sectional, two-dimensional view showing a second plane through the volume in which the longitudinal axis defined by the virtual needle lies, the second plane being different from the first plane. Thus, in some examples, the first and second cross-sectional, two-dimensional views can include the needle axis.

In some examples, changing between the first cross-sectional, two-dimensional view and the second cross-sectional, two-dimensional view can be a result of a received command to rotate the volume about the longitudinal axis defined by the virtual needle in order to adjust the view of the volume.

Aspects of the disclosure can include methods for planning an ablation procedure prior to performing an ablation procedure involving a needle inserted into a volume. Some such methods can include receiving volumetric image data including data representative of the location of the needle in the volume and segmenting the needle in the volumetric image data, including determining a location of the needle in the volume. The method can include generating and displaying a first cross-sectional, two-dimensional view of the volume, the first cross-sectional view showing a first plane through the volume in which the needle lies, and generating and displaying a second cross-sectional, two-dimensional view of the volume. The second cross-sectional view can show a second plane through the volume in which the needle lies, and the second plane can be different from the first plane.

Aspects of the disclosure can also include methods for performing an ablation procedure after an ablation needle is inserted into a volume of patient tissue. Some such methods can include receiving volumetric image data representing the volume of patient tissue including the ablation needle, and segmenting the ablation needle in the volumetric image data. The segmenting can include determining a location of the ablation needle in the volume, and the ablation needle can define axis extending through the volume.

The method can further include generating and displaying a first cross-sectional view of the volume, the first cross-sectional view showing a first plane through the volume in which the axis defined by the ablation needle lies and generating and displaying a second cross-sectional view of the volume. The second cross-sectional view can show a second plane through the volume in which the axis defined by the ablation needle lies, wherein the second plane is different from the first plane.

In various such methods, additional features, such as identified lesions, treatment volumes (e.g., volumes of ablated tissue, iceballs), simulated treatment volumes, isotherms, simulated isotherms, organ boundaries and the like, can be similarly segmented and displayed in various cross-sectional views. Some aspects of the disclosure include non-transitory computer-readable media comprising executable instructions for causing one or more programmable processors to perform one or more such methods.

Some aspects of the disclosure include systems, such as ablation systems including an ablation needle or other ablation probe, including an imaging system, a display, and a processing system. The processing system can be configured to receive a plurality of two-dimensional images of the patient tissue and generate volumetric image data of the patient's tissue based on the received plurality of two-dimensional images. The processing system can further segment the ablation needle within the volumetric image data of the patient's tissue.

During an ablation process, the processing system can be configured to predict a temperature profile of the patient's tissue proximate the ablation needle and identify one or more volumetric isotherm boundaries based on the predicted temperature profile. In some such systems, the processing system can be configured to display a cross-sectional image of the volumetric image data on the display, the cross-sectional image showing a plane that includes an axis defined by the ablation needle and including the needle and one or more of the identified one or more volumetric isotherm boundaries.

In this disclosure, although cryoabaltion is used as an example of an ablation modality, the invention is equally applicable to any ablation modality in which a volume of tissue is ablated. Such modalities include thermal ablation modalities, (those in which tissue temperature is raised in order to carry out the ablation, such as radiofrequency ablation and microwave ablation, and cryoablation), and other modalities including electroporation modalities, such as irreversible electroporation and ultrasound based modalities, such as high-intensity focused ultrasound ablation. Although "needles" are referred to through out this specification the invention is not so limited, and other ablation probes may also be used. Such probes may be blunt ended or be adapted to penetrate tissue, such as by having a sharp tip.

BRIEF DESCRIPTION OF THE DRAWINGS

FIG. 14A shows an iceball formed by a single needle.

FIG. 14B shows an iceball formed by a pair of cryoneedles.

FIG. 14C shows an iceball formed by three cryoneedles.

DETAILED DESCRIPTION

Cryosurgical systems can be used for cryoablating target tissues (e.g., a tumor). Typically, such systems include one or more cryoprobes, one or more cryofluid sources and a control system. The cryofluid sources can supply gases such as argon, nitrogen, air, krypton, $CO_2$, $CF_4$, xenon, and various other gases that are capable of reaching cryogenic temperatures (e.g., temperatures below 190 Kelvin) when expanded from pressures greater than about 1000 psi. As used herein, "cryofluid" can refer to any fluid that reaches low temperatures (e.g., below 190 Kelvin) when expanded from pressures greater than about 1000 psi (e.g., typically around 3500 psi). The cryosurgical system can also include a control system having one or more sensors, flow meters, timers, analog/digital converters, wired or wireless communication modules, etc. Additionally, the control system can also regulate the flow rate, temperature and pressure of cryofluid supplied to the cryoprobe.

During cryosurgery, for instance, a surgeon may deploy one or more cryoprobes to cryoablate a target area of a patient anatomy by placing the cryoprobe at or near the target area of the patient anatomy. In one example, cryoprobe utilizes the Joule-Thomson effect to produce cooling or heating. In such cases, a cryofluid expands in the cryoprobe from a higher pressure to a lower pressure. Expansion of the cryofluid results in temperatures at or below those necessary for cryoablating a tissue in the vicinity of the tip of the cryoprobe. Heat transfer between the expanded cryofluid and the outer walls of the cryoprobe can be used to form an iceball, and consequently cryoablate the tissue.

Figure 1A:
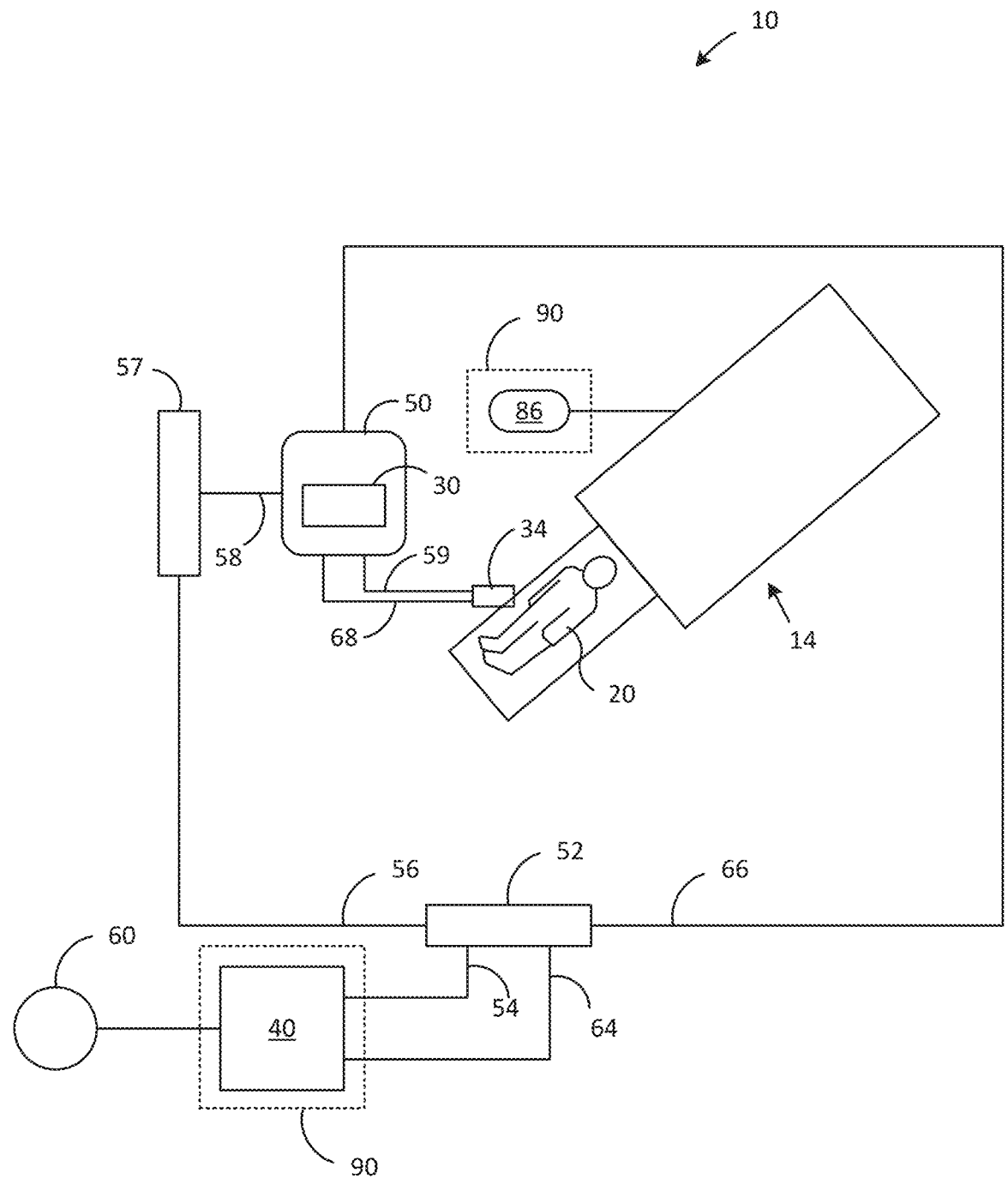
FIG. 1A is a schematic of a volumetric imaging guided cryosurgery system 10 according to a non-limiting exemplary embodiment.

FIG. 1A is a schematic of a volumetric imaging guided cryosurgery system 10 according to a non-limiting exemplary embodiment. The system includes a volumetric image scanner 14, for example, a computed tomography (CT) scanning system, a magnetic resonance imaging (MRI) system, or the like, that can be configured for accommodating a patient 20.

In some examples, the volumetric imaging system may image the patient before insertion of one or more surgical tools 34 to visualize patient areas of interest, such as a tumor or a patient cavity. Further, imaging may be performed during insertion to guide the surgical tool to the intended location inside the patient. Additionally, imaging may be performed after insertion and during surgery, as well as after surgery.

System 10 can include a control system 40 in communication and configured to facilitate operation of surgical tool 34, for example, via a connector interface 30. A variety of electrical and fluid connections can exist between the control system 40 and the surgical tool 34 in order to facilitate operation of the surgical tool 34. In an exemplary embodiment, control system 40 can be electrically connected to a junction box 52 by way of a first electrical connection 54. Further, the junction box 52 can include a second electrical connection 56 to connect to electrical and/or imaging equipment 57 (such as an imaging router and electrical filters). A third electrical connection 58 may connect the electrical and/or imaging equipment 57 to the connector interface 30 and/or mobile cart 50. The junction box 52 can permit removable electrical connection between various components.

Referring again to FIG. 1A, in some examples, the system may be used to perform many types of surgical procedures, and the systems and methods disclosed herein should not be construed as limiting to any one type of surgical procedure, such as cryosurgical procedures.

In certain examples, the surgical system can be a cryosurgery system, such as a cryoablation system. Accordingly in some examples, the system may include one or more cryofluid source 60, for example, under the control of control system 40. For instance, control system 40 may communicate with one or more components, such as pumps and/or valves, to direct cryofluid from the cryofluid source 60 to various locations within the system, such as to surgical tool 34. The cryofluid source can be a liquid or gas container.

Cryofluid may be delivered at cryogenic temperatures and pressures to surgical tool 34 (e.g., cryoprobes). The cryofluid source can be a cooling gas such as argon, nitrogen, air, krypton, $CF_4$ xenon, or $N_2O$.

The control system may be configured to deliver cryofluid to a cryoprobe at cryogenic temperature for cooling and/or freezing a patient's tissue and at a non-cryogenic temperature to cool the cryoprobe or a portion or component thereof. In some cryoprobes the cryofluid can be delivered to the cryofluid supply as described elsewhere herein. In various embodiments, exemplary connections and/or communication between various components can be employed, for example, such as described in U.S. Provisional Patent Application No. 62/585,262, filed Nov. 13, 2017, and entitled "CRYOABLATION SYSTEM WITH MAGNETIC RESONANCE IMAGING DETECTION," which is assigned to the assignee of the instant application and is hereby incorporated by reference.

Referring back to FIG. 1A, a system may also include a visualization system 86 operatively coupled to a volumetric image scanner 14, such as a CT scanner, for generating and/or displaying an image representative of an anatomical feature of a patient 20, for example, to provide guidance to a surgeon during surgery. The visualization system 86 can include or otherwise communicate with one or more displays configured to present such information to a system user, and can include an interface to receive inputs from a user.

In various examples, visualization system 86 and control system 40 can operate independently, or may operate together. For instance, in some embodiments, visualization system 86 and control system 40 are capable of interfacing with one another and/or performing similar functions as each other. Such a configuration may facilitate both system control (e.g., control of surgical tool 34) and visualization (e.g., visualization of information relating to the operating conditions of and/or data generated by the overall system) by a user of the system. In such cases, the visualization system 86 may enable a surgeon to select a desired image, for example, to monitor the progress of the surgical process, images relating to guidance and/or current information relating to one or more surgical tool 34.

In some examples, visualization system 86 and/or control system 40 can be included in a processing system 90. In some embodiments, processing system 90 can generally include one or more processors configured to carry out one or more operations described with respect to the visualization system 86 and/or the control system 40. For example, processing system 90 can be configured to interface with surgical tool 34 for performing a surgical procedure and with volumetric image scanner for receiving volumetric image data. In some examples, processing system includes separate visualization system 86 and control system 40 portions, which can be in separate, distributed components. In other examples, both the visualization system 86 and the control system 40 can be embodied as a single component.

In general, the processing system can include or be embodied as one or more processors configured to process information, such as volumetric image data (e.g., from volumetric image scanner 14) and control operation of one or more system tools, such as surgical tool 34, volumetric image scanner 14, or the like, for example, in response to one or more commands.

One or more processors configured for processing and/or control processes can be embodied in a stand-alone computer. In some such embodiments, such a stand-alone computer can be configured to receive volumetric image data, either directly from a volumetric image scanner or via upload or download of such data. Additionally or alternatively, such a stand-alone computer can be configured to control operation of one or more system components, such as volumetric image scanner 14 and/or surgical tool 34.

In various examples, the one or more processors in the processing system can be embodied as one or more components located on-site (e.g., in the same location as volumetric image scanner 14 and surgical tool 34). Such components can include, but are not limited to, application specific integrated circuits (ASICs), microcontrollers, microprocessors, field-programmable gate arrays (FPGAs), or any other appropriate structure capable of receiving and processing data. Additionally or alternatively, one or more processors can be distributed across a network and be configured to receive and process volumetric image data and control system operation as described herein from a remote location. For instance, in some examples, processor can include cloud-based computing capabilities.

Figure 1B:
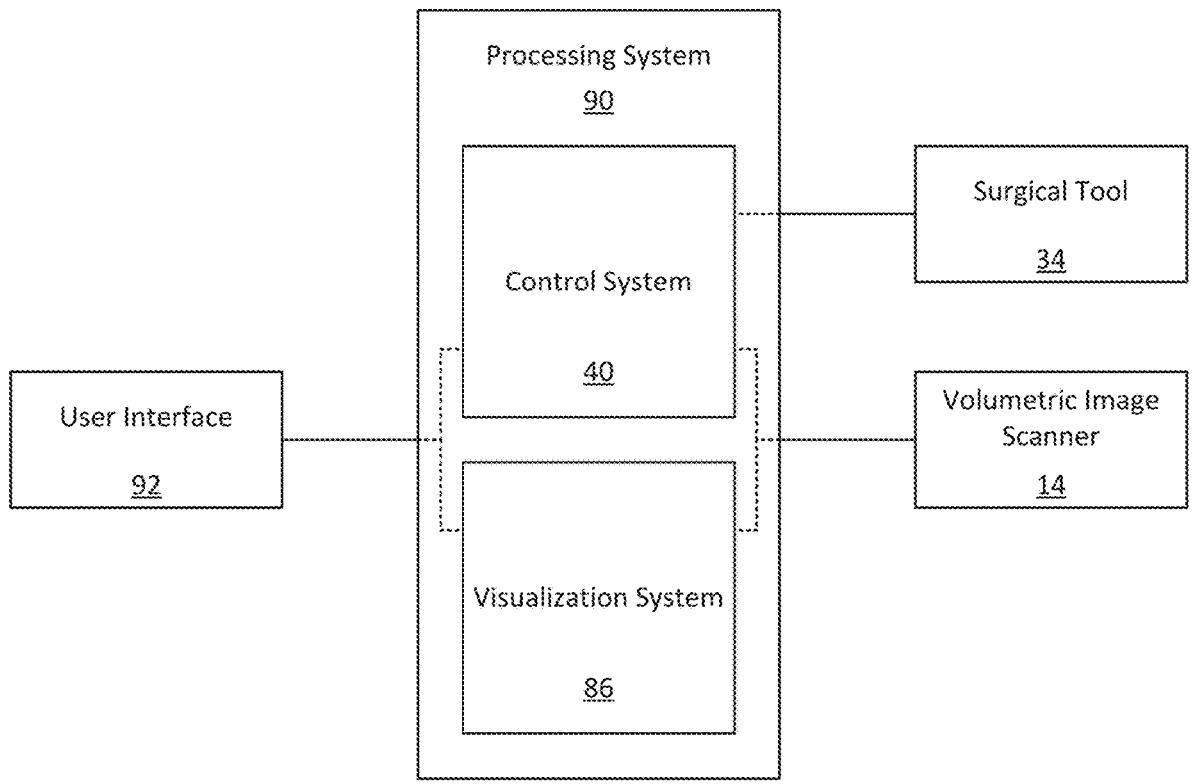
FIG. 1B shows an exemplary schematic communication interface between a processing system and other system components.

FIG. 1B shows an exemplary schematic communication interface between a processing system and other system components. In the illustrated example, processing system 90 is in communication with surgical tool 34, volumetric image scanner 14, and a user interface 92. In some embodiments, processing system 90 can be configured to control operation of surgical tool 34, for example, by controlling the application of electrical power, cryofluid, or other resources to the surgical tool 34. In some examples, the processing system 90 can be configured to start, stop, or adjust operation of the surgical tool 34. As described elsewhere herein, in some examples, processing system 90 includes a control system 40 configured to control surgical tool 34.

As shown, the processing system 90 is further in communication with a volumetric image scanner 14. In various examples, the processing system 90 can be configured to control operation of the volumetric image scanner 14, for example, by initiating a volumetric image scan (e.g., of a patient). Control of the volumetric image scanner 14 can be initiated, for example, via the control system 40 of the processing system 90. In the illustrate example, processing system 90 includes a visualization system 86 in communication with the volumetric image scanner 14. The visualization system 86 can be configured to receive volumetric image data from the volumetric image scanner 14 and process the received volumetric image data from presentation on a display.

The processing system 90 is in communication with a user interface 92, which can enable communication between the processing system 90 and a user. For example, in various embodiments, a user may control one or more operating parameters of a surgical tool 34 via the user interface 92. Additionally or alternatively, user interface 92 may be used to communicate information from the processing system 90 to a user, for example, via a display. In various examples, user interface 92 can be embodied as a computer workstation (e.g., including control system 40 and/or visualization system 86) that provides a system with both input (e.g., via a standard mouse and keyboard) and output (e.g., via a display) capabilities. Additionally or alternatively, a user interface 92 can include a remote device, such as a smartphone or tablet interface allowing a user to interface with the system 10. In general, the user interface 92 can include one or more components in communication (e.g., wired or wireless communication) with other system components in order to interact with the system.

Figure 2:
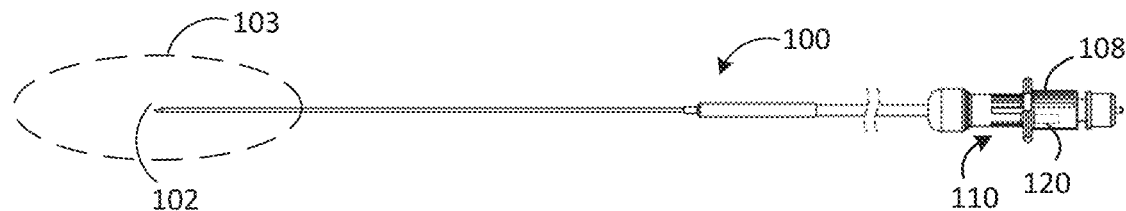
FIG. 2 is a front view of an exemplary cryoprobe.
Figure 3:
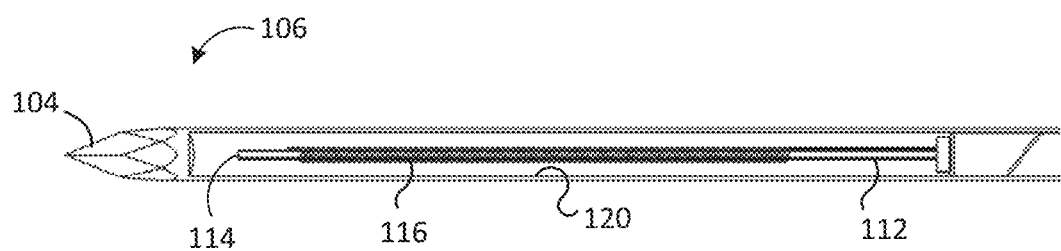
FIG. 3 is a sectional front view of the cryoprobe of FIG. 2.

As described elsewhere herein, a surgical tool can be a cryoprobe 100 in a non-limiting exemplary embodiment. FIG. 2 is a front view of one such cryoprobe 100 and FIG. 3 is a sectional front view of the cryoprobe 100 of FIG. 2. Referring to FIGS. 2 and 3, the cryoprobe 100 can include an elongate body. Components of the cryoprobe 100 can be located within a probe shaft 102. The cryoprobe can, in some cases, be a cryoneedle. The probe shaft 102 can terminate in a distal operating tip 104 disposed at a distal section 106 of the cryoprobe 100 for penetrating through tissues of a patient 20 during deployment. In embodiments where the cryoprobe is configured as a cryoneedle, the distal operating tip 104 can penetrate the patient's skin. In alternate embodiments, the cryoprobe can be a flexible probe, and may be inserted by way of a catheter. A proximal coupler 108 can facilitate connections of the cryoprobe 100 to a connector interface 30, control system 40 and/or cryofluid source.

The probe shaft 102 can be of substantially thin cross section to allow deployment in tissues of a patient 20. In an example, the cryoprobe can be a cryoneedle, having a probe shaft 102 outer diameter of about 2.1 millimeters. Other dimensions of the probe shaft 102 are also contemplated. For example, the probe shaft 102 can have an outer diameter of between about 1.5 millimeters and about 2.4 millimeters. In addition, in embodiments where the cryoprobe is a cryoneedle, the distal operating tip 104 can be made of a pliant material so as to be flexible (e.g., relative to the proximal portion of the cryoprobe 100) for penetrating soft tissue. Alternatively, a substantial portion of the cryoprobe can be generally flexible and may not pierce the patient skin, and may be flexible (bendable) about its central axis, by a desired angle.

As seen in FIG. 3, the cryoprobe 100 includes a cryofluid supply 112 extending substantially along its length for providing a high-pressure cryofluid to the distal operating tip 104. The cryofluid supply 112 can be positioned coaxially/concentrically within the probe shaft 102. The cryofluid supply 112 can be configured to supply a cryofluid for forming iceballs (e.g., shown as 103 in exemplary FIG. 2) on an outer surface of the probe shaft 102 over the distal section 106. In some cases, the cryofluid supply 112 can be a capillary tube.

With continued reference to FIG. 3, in some examples, the cryoprobe 100 includes a cryocooler. For instance, in the illustrated example, the cryofluid supply 112 can terminate in a Joule-Thomson orifice 114. The Joule-Thomson orifice 114 can be positioned near the distal operating tip 104, so as to permit cryofluid exiting the Joule-Thomson orifice 114 to expand into an expansion chamber. Accordingly, a high-pressure cryofluid supplied via the cryofluid supply 112 exits through the Joule-Thomson orifice 114 and expands in the expansion chamber. As the cryofluid expands in the expansion chamber, it cools rapidly and forms iceballs of different shapes and/or sizes over the outer surface of the distal operating tip 104. The expansion of the cryofluid can be such that when expanded, the cryofluid is colder than the incoming cryofluid. While an exemplary cryocooler such as a Joule-Thomson orifice 114 is illustrated, it should be understood that other types of cryocoolers such as cryogenic dewars, Stirling-type cooler, pulse-tube refrigerator (PTR), Gifford-McMahon (GM) cooler, and the like are contemplated within the scope of the present disclosure. Further, as briefly noted above, cryofluids which may be used for cooling include argon, liquid nitrogen, air, krypton, $CF_4$, xenon, or $N_2O$.

Referring again to FIG. 3 for illustrative purposes, in some examples, a heater 116 can optionally be provided within the probe shaft 102 to facilitate thawing and/or cauterizing tissue. In some such examples, the heater 116 may be operated after cooling and iceball formation to thaw frozen tissue to facilitate disengagement of cryoprobe 100 therefrom. As illustrated in this exemplary embodiment, an electrical heater 116 can be provided coaxially with the cryofluid supply 112 and the probe shaft 102 to facilitate heating the distal section 106 of the cryoprobe 100. Alternatively, the electrical heater 116 can be positioned elsewhere in cryoprobe 100 to heat the distal section 106 of the cryoprobe 100. The electrical heater 116 can be a resistive heater 116 and can include a helically-wound electrical wire which can generate heat proportional to the current flow therethrough and the electrical resistance of electrical heater 116. In such cases, as alluded to previously, the control system 40 (shown in FIG. 2) can supply and/or regulate electrical current flow to the electrical heater 116 within the cryoprobe 100.

In some systems, the control system comprises or otherwise communicates with one or more temperature sensors configured to measure the temperature of the surgical tool or a component thereof. For instance, the control system can include or communicate with a temperature sensor for measuring temperature of the distal section 106 of the cryoprobe 100, or of the cryoprobe shaft or of an electronic chip or of an electrical heater. Temperature measurement may be performed before, during or after placement inside the patient to monitor probe temperature or the temperature of any of its components, for example measurement may occur during placement and/or during a surgical procedure (e.g., thaw or cautery procedure) or before the procedure, whilst the system is being set up or prepared for use. In an example, the temperature sensor can comprise resistive materials whose electrical resistance may change when temperature thereof changes (e.g., a positive temperature coefficient material). The change in resistance can be measured by the control system 40, and consequently, the temperature change be determined by the control system 40 based on known correlations between resistance and temperature for the specific type of material. Likewise, the temperature of the electrical heater may also be determined in this manner.

As described elsewhere herein, the cryoprobe 100 comprises electrical heater 116. Accordingly, in certain advantageous embodiments the materials of the electrical heater 116 (such as the heater 116 wire) can perform dual functions of resistively heating the probe shaft 102 when current flows therethrough, and providing temperature feedback to the control system 40 during probe heating. Electrical heaters may also be provided with a needle heating element fault detection circuitry. Such circuitry may be operatively connected to the control system for the purposes of fault detection. The control system may be configured to "blank" or ignore signals from this fault detection circuitry in the presence of an operative MRI system as described further herein.

In some advantageous examples, referring back to FIG. 1A, the surgical tool 34 may include electronic components that permit identification thereof when connected to the connector interface 30 and/or mobile cart 50. In an example, the surgical tool is a cryoprobe 100 as illustrated in FIGS. 2 and 3. The cryoprobe 100 may include an electronic chip 120 that may be positioned in the proximal portion (e.g., near the proximal connector) of the tool. However, in various examples, the surgical tool can include an electronic chip 120 anywhere along its body. The electronic chip 120 can include a non-transitory data storage medium that can be machine readable. Electrical connections between the connector interface 30 and/or mobile cart 50, and the control system 40 may permit the control system 40 to have read/write access of the electronic chip 120.

The electronic chip 120 can permit identification of the surgical tool when multiple surgical tools are connected to the mobile cart 50. For example, each electronic chip 120 can store a unique surgical tool identifier in its memory, and may thereby permit identification of the surgical tool connected to a particular connector port on the connector interface 30. Additionally, the electronic chip 120 may store other information, such as the duration over which a particular surgical procedure was performed, the total amount of time during which the surgical tool was used, and the like. Further, such information may be transmitted (e.g., via electrical connections) to the control system 40.

In embodiments, volumetric imaging systems may be used simultaneously, or periodically at various points during a cryosurgical procedure, for example, as described with respect to MRI imaging and cryosurgical procedures in U.S. Provisional Patent Application No. 62/585,262, which is incorporated by reference. In general, many different volumetric imaging technologies may be used. As described above, volumetric imaging techniques can be used to acquire image information before, during, and/or after a procedure. However, traditional imaging processes may be limited in the information provided to a user, and expert knowledge and/or assumptions are necessary to obtain desired information even from volumetric image data.

Figure 4:
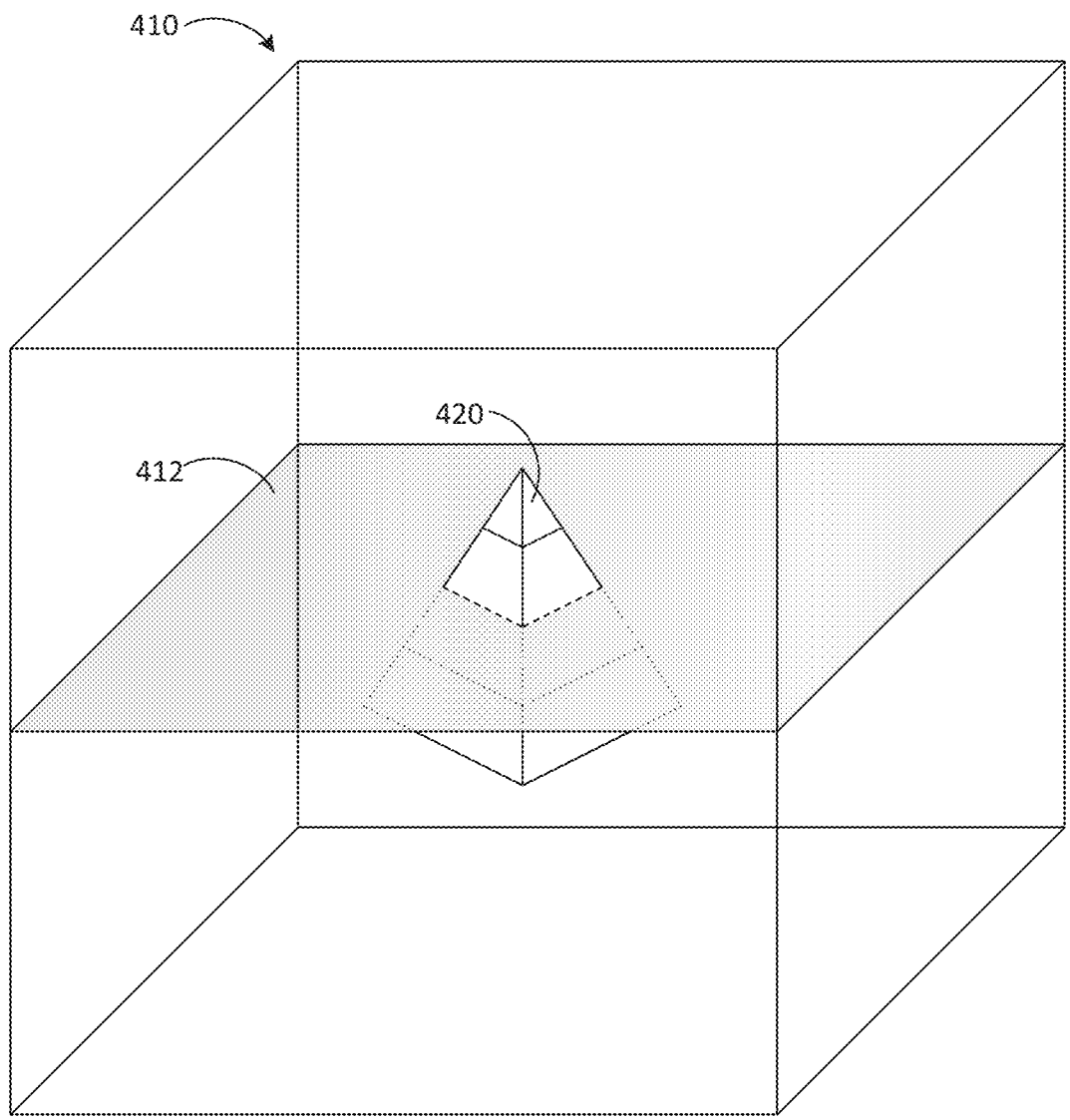
FIG. 4 is a simple geometric sketch showing an exemplary volumetric imaging process.

FIG. 4 is a simple geometric sketch showing an exemplary volumetric imaging process. In the illustrated example, volume 410 includes object 420 contained therein. Plane 412 is shown extending through the volume 410 and intersecting with object 420. In an exemplary volumetric imaging process, a volume 410 is represented by stack including a plurality of parallel, two-dimensional slices, such as plane 412. Thus, each image corresponds to a different "depth" within the volume 410. Viewing objects within the volumetric images often corresponds to selecting one of such slices and viewing the cross-sectional image at that depth, or moving up or down within the volume to different depths to view different cross-sections.

However, if each cross-sectional slice is generally parallel to the others, it can be difficult to view objects having a dimension of interest (e.g., a longest dimension and/or a cross-sectional plane) that lie at an angle relative to the image slices generally available for viewing. For example, object 420 in the volume 410 in FIG. 4 is a square pyramid, and the intersection of plane 412 with object 420 will be approximately square. Moreover, every cross-section of object 420 taken at planes parallel to plane 412 (e.g., 2-dimensional slices) will also show an approximately square cross-section. It would therefore require viewing several such images taken at several planes to deduce the approximate shape of the volume 410.

Figure 5A:
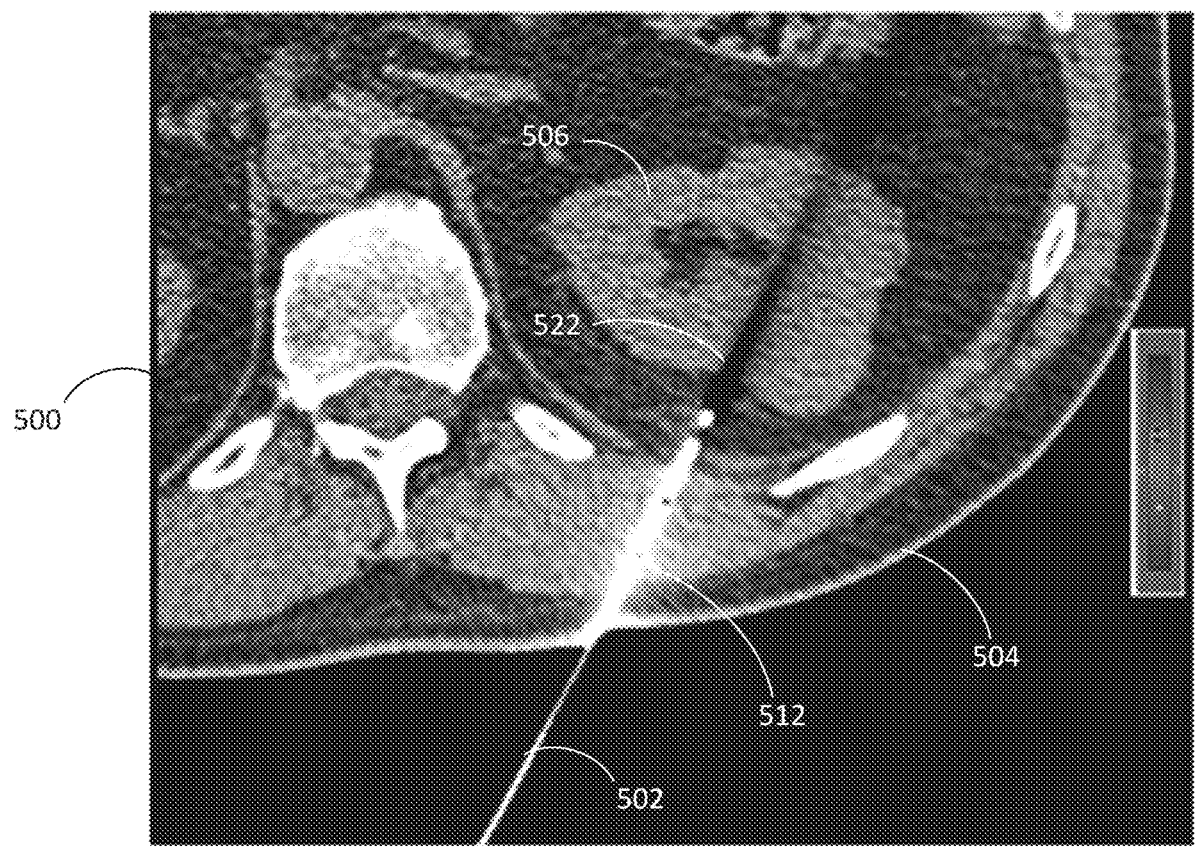
FIG. 5A shows an exemplary cross-sectional image of a patient and a needle (e.g., a cryoneedle) inserted into the patient.

During an exemplary treatment process, such limited viewing capability can limit not only the ability to observe structures (e.g., object 420) within the volume, but may also inhibit the ability to view various additional features that may be within the volume, for example, for a treatment process. FIG. 5 shows an exemplary cross-sectional image of a patient and a needle (e.g., a cryoneedle) inserted into the patient.

In the illustrated example of FIG. 5, the cross-sectional image 500 shows a needle 502 inserted into a patient volume 504, for example, to perform one or more processes with respect to a lesion 506 (e.g., to biopsy or apply treatment to the lesion 506). In the cross-sectional view 500, the view of the needle 502 includes a first section 512 and a second section 522. The first section 512 appears dark in color, while the second section 522 appears light in color. The color differences between the first section 512 and second section 522 correspond to such portions of the needle 502 being in and out of the imaging plane for cross-sectional image 500. That is, in an exemplary view, the first section 512 of needle 502 lies within the plane of cross-sectional image 500. However, the second section 522 of the needle 502 lies outside of the plane, and therefore appears different than the first section 512 of the needle 502 that lies within the plane.

Figure 5B:
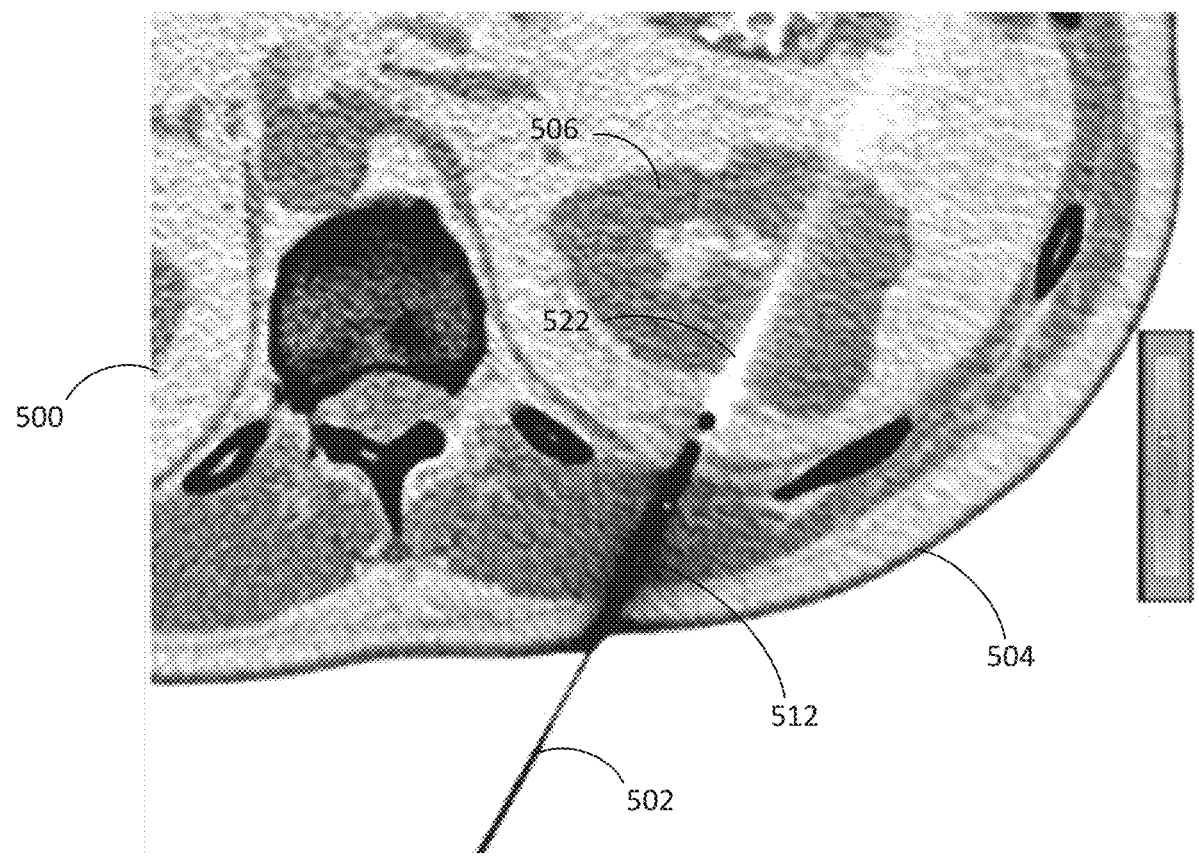
FIG. 5B shows an inverse-color version of FIG. 5A for convenience of viewing.

Thus, when viewing cross-sectional image 500, a system user (e.g., a clinician) may not be able to tell where in the volume the needle 502 terminates, for example, whether the tip of the needle lies above or below the plane of the image. This can decrease the ability to perform a desired operation using the needle 502 (e.g., a biopsy, a tissue destruction process, etc.). Transitioning between different cross-sectional viewing planes (e.g., up or down within the volume) may help a user understand more information, such as whether the needle 502 is angled upward or downward, however, in some such examples, if the needle 502 is not parallel to the imaging planes, a user may not be able to view the entire needle within the cross-sectional image. FIG. 5B shows an inverse-color version of FIG. 5A for convenience of viewing.

Figure 6:
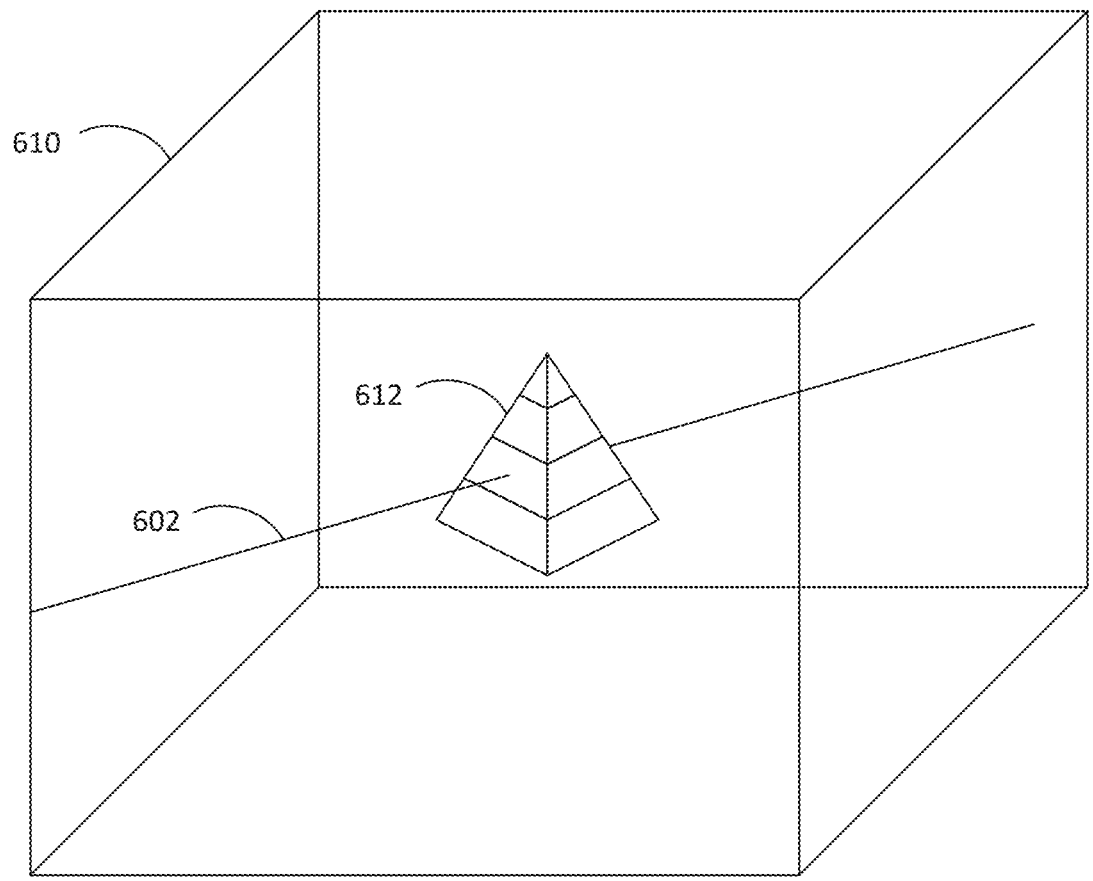
FIG. 6 is a simple geometric representation showing an exemplary volume similar to that of FIG. 4

FIG. 6 is a simple geometric representation showing an exemplary volume similar to that of FIG. 4. In the illustrated example of FIG. 6, volume 610 includes object 620 contained therein. Axis 602 extends through the volume 610 and intersects object 620. In some examples, rather than a volume being segmented by parallel planes (e.g., volume 410 and planes parallel to plane 412 in FIG. 4), an axis 602 can define many planes within volume 610 (e.g., planes rotated about axis 602 in which axis 602 lies). In various volumetric imaging processes, axis 602 can be defined virtually or can be defined based on an object in an imaged volume, such as a needle within a patient.

Figure 7A:
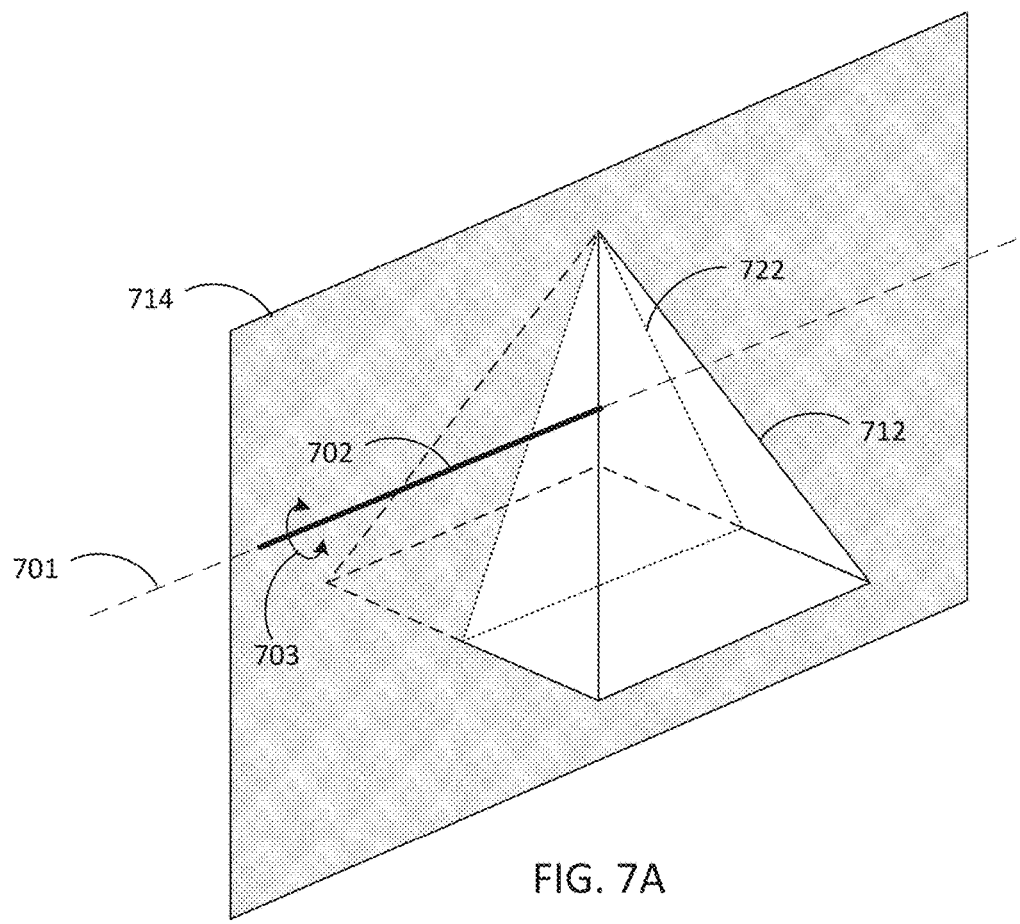
FIGS. 7A and 7B show exemplary planes in a volume that can be defined by an axis extending therethrough.
Figure 7B:
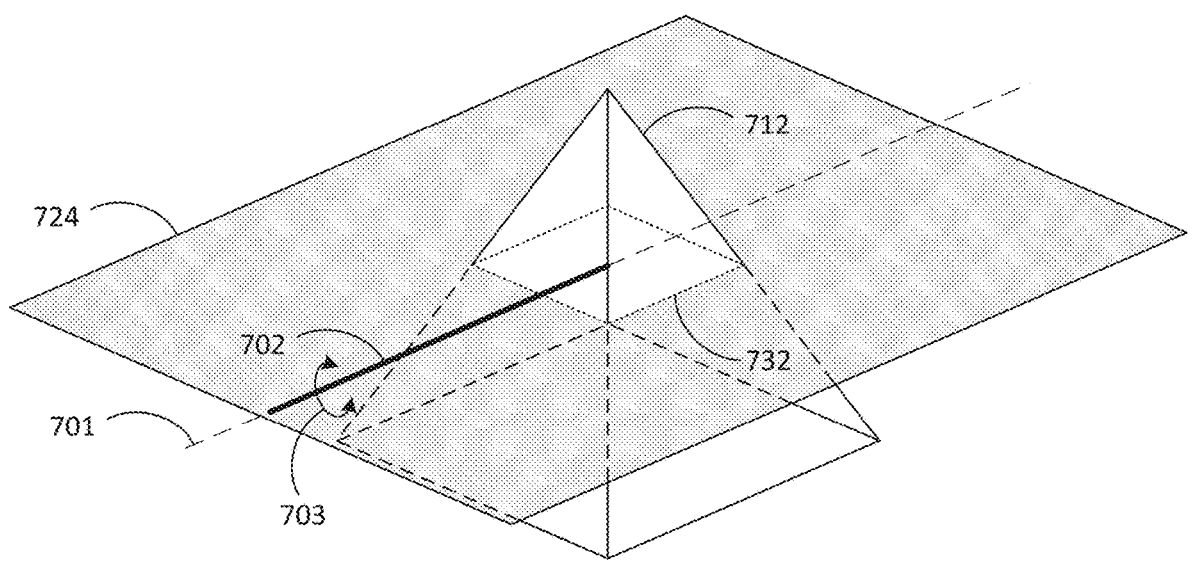

FIGS. 7A and 7B show exemplary planes in a volume that can be defined by an axis extending therethrough. FIG. 7A shows an axis 701 extending through a three-dimensional object 712 having a pyramid shape. As described, an axis extending through a volume can define a plurality of planes within the volume. In the example of FIG. 7A, axis 701 lies in a plane 714, which intersects object 712 at intersection 722.

Within the context of volumetric imaging, and in particular, in a medical setting, needle 702 may lie along axis 701. Needle 702 may be a virtual needle placed in the volume, or may be a physical needle present within a patient's imaged tissue. In the case of a virtual needle 702, in some examples, the virtual needle 702 can be manually or automatically placed at a location within the volume in, and the location of the placed needle 702 can define the axis 701. In the case of an imaged physical needle 702, image (e.g., volumetric image) processing techniques can be used to identify and segment the needle 702 in the image data in order to identify the axis 701 along which the needle 702 extends.

As noted, an axis 701 can define a plurality of planes in which the axis 701 lies, for example, by rotating the plane 714 about the axis 701, such as illustrated by arrow 703. In the illustrated example of FIG. 7A, the plane 714 intersects volumetric object 712 at intersection 722. In this example, the shape of the intersection of plane 714 and the object 712 is triangular, axis 701 extends through the triangular intersection 722, and needle 702 extends into the triangular intersection 722.

In the example of FIG. 7B, needle extends into the volumetric object 712 along axis 701 as shown in and described above with respect to FIG. 7A. However, in contrast to FIG. 7A, in the example of FIG. 7B, a different plane (plane 724) including axis 701 and needle 702 is shown intersecting object 712. While the object 712 in FIG. 7B is the same pyramid shape as shown in FIG. 7A, the intersection 732 of plane 724 and object 712 is a square. That is, the cross-sectional image taken at plane 724 in FIG. 7B would show an object 712 having a square shape, while the cross-sectional image taken at plane 714 in FIG. 7A would show object 712 having a triangular shape. However, since the plane is defined to include the axis 701, and therefore the needle 702, the entire length of the needle will be present within the plane (414, 724) and any corresponding cross-sectional image.

Switching between the views of FIGS. 7A and 7B allows for viewing of the volume surrounding the needle 702 from various perspectives while maintaining a view of the needle itself. In the illustrated example, a user viewing the cross-sectional images of FIGS. 7A and 7B will be provided with information representative of the volume surrounding the needle 702, including the volumetric shape of object 712, which may be difficult to interpret from viewing traditional parallel cross-sectional images or otherwise require significant expertise of volumetric image viewing and analysis.

As described elsewhere herein, in some examples, a processing system (e.g., including visualization system 86) can include one or more processor configured to process volumetric image data, for example, produced via volumetric image scanner 14. In some examples, processing the volumetric image data comprises treating the volumetric image data as a volume of data rather than a plurality of individual two-dimensional image slices. For example, volumetric image data processing can include steps such as cross-sectioning the volumetric image data in any of a plurality of planes in order to construct a custom two-dimensional visualization of a portion of the volumetric image data. Volumetric image processing can further include steps such as identifying features (e.g., feature boundaries) and segmenting such features (e.g., determining which voxels in the volumetric image data belong to a given feature) within the volumetric image data. In various examples, feature identification can be performed using one or more techniques, such as any of a variety of feature/boundary detection image processing techniques. In some examples, a user may manually identify one or more features in volumetric image data.

For example, with respect to FIGS. 7A and 7B, a visualization system can receive volumetric image data of a volume including object 712, needle 702, and planes 714 and 724. In some embodiments, the visualization system can be configured to analyze the volumetric image data and segment one or more objects therein, such as needle 702, object 712, or the like. In some examples, the visualization system can segment the needle 702 and identify an axis 701 extending through the volume that approximates the longitudinal dimension of the needle 702. In some such examples, a perfectly straight needle 702 may extend directly along axis 701, however, if a needle 702 is slightly bent, for example, having been bent during insertion, an axis 701 may be identified that approximates the longitudinal direction of the needle 702.

In some examples, the visualization system can be configured to generate a 2-dimensional cross-sectional of the volume showing a plane of image data in which the defined axis 701 lies. For example, with reference to FIG. 7A, the visualization system can be configured to identify axis 701, and can generate a cross-sectional image showing plane 714, in which the axis 701 and needle 702 lie. Similarly, the visualization system can be configured to identify axis 701, and can generate a cross-sectional image showing plane 724, in which the axis 701 and needle 702 also lie. In still further examples, the visualization system includes or communicates with an interface (e.g., user interface 92) by which a user may manipulate the displayed cross-sectional image by selecting a plane in which the identified axis 701 lies. For example, in an exemplary implementation, a user may effectively rotate the view about the axis 701 in order to select a new cross-sectional image in which the axis 701 lies, such as reflected by arrow 703.

With reference to FIGS. 7A and 7B, a user may transition from cross-sectional view of FIG. 7A, showing plane 714, to the cross-sectional view of FIG. 7B, showing plane 716, by rotating the view from plane 714 to plane 724. In the case of FIGS. 7A and 7B, in which the volume includes object 712, transitioning from viewing plane 714 to viewing plane 724 would result in observing a change from intersection 722 of object 712 with plane 714 to intersection 732 of object 712 with plane 724.

Figure 8A:
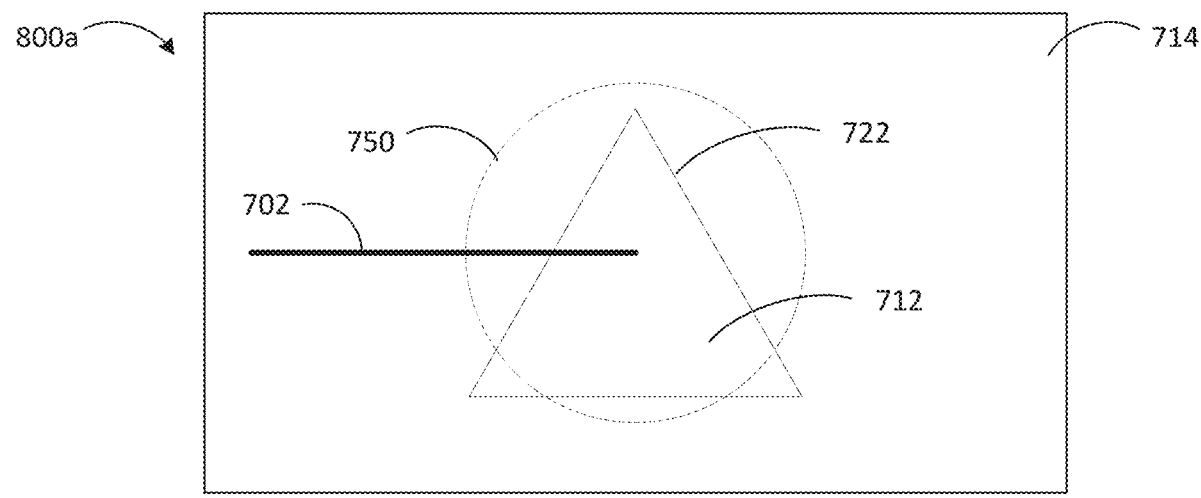
FIGS. 8A, 8B, and 8C show exemplary cross-sectional views of plane 714 of FIG. 7A.
Figure 8B:
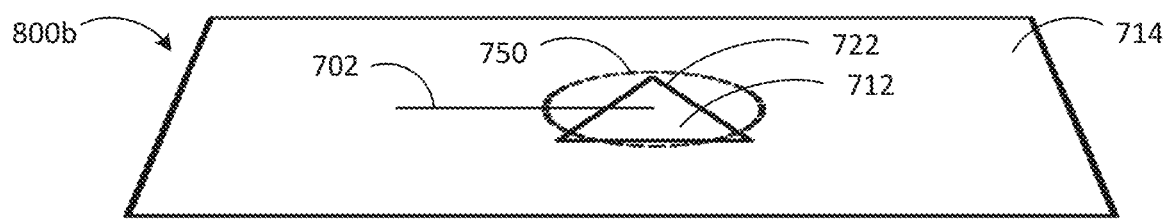
Figure 8C:
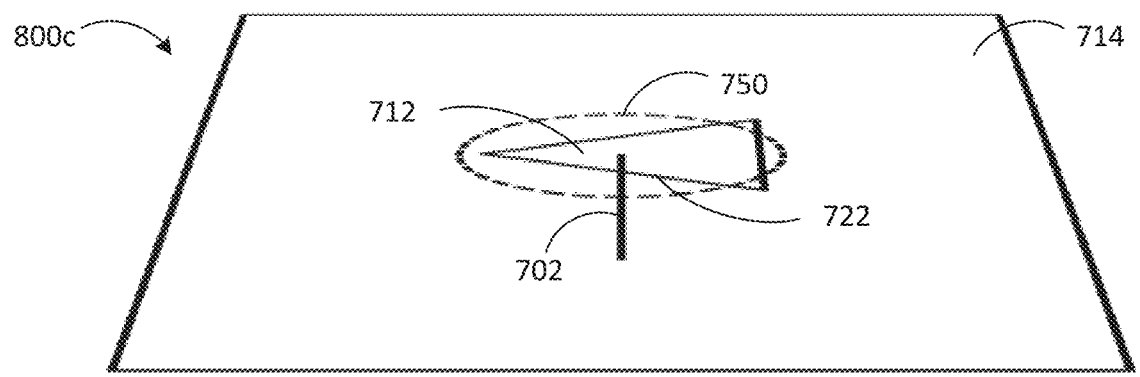

In some embodiments, visualization system can display a cross-sectional image including an axis in a variety of ways, including as a plan view, a perspective view, or the like. In some examples, a user may adjust the orientation and elevation of the view of the cross-sectional image. FIGS. 8A-8C show exemplary cross-sectional views of plane 714 of FIG. 7A. Cross-sectional views 800*a*, 800*b*, and 800*c* each show the needle 702 and the intersection 722 of the object 712 and the plane 714. In various embodiments, a visualization system can be configured to present a default view (e.g., one of views 800*a-c*), or can prompt a user to select a view (e.g., from a list of available views).

Figure 9A:
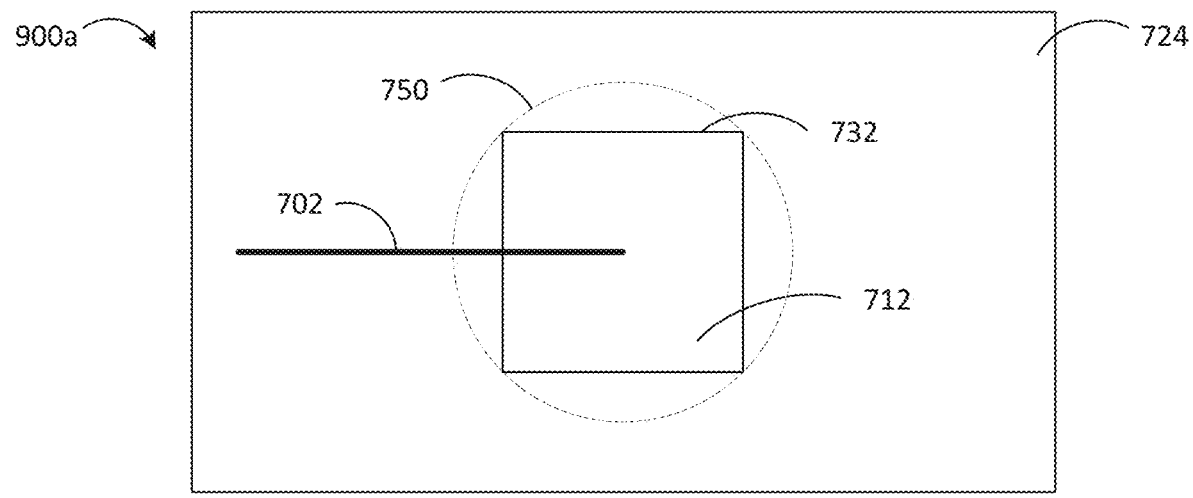
FIGS. 9A, 9B, and 9C show exemplary cross-sectional views of plane 724 in FIG. 7B.
Figure 9B:
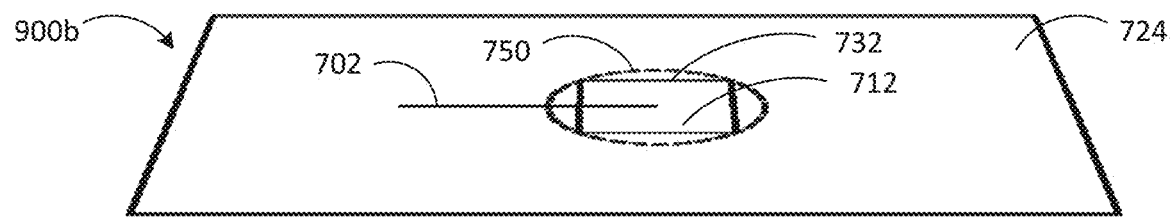
Figure 9C:
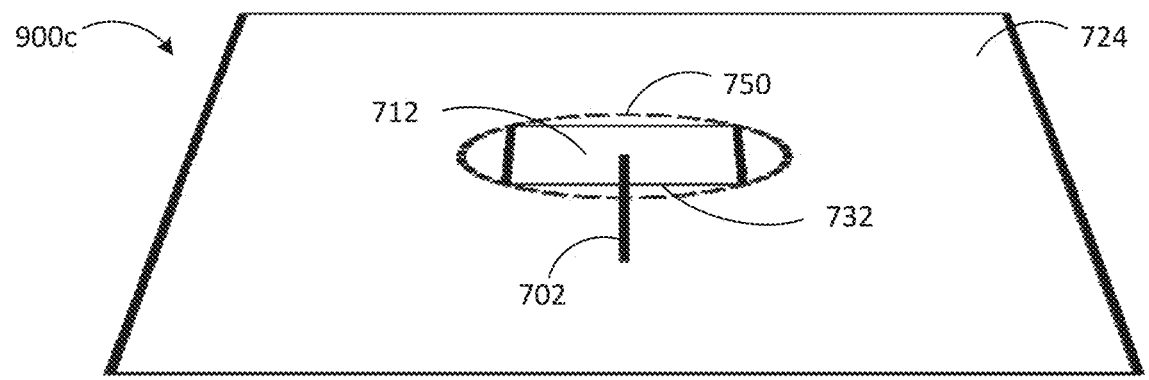

Similarly, FIGS. 9A-9C show exemplary cross-sectional views of plane 724 in FIG. 7B. Cross-sectional views 900*a*, 900*b*, and 900*c* each show the needle 702 and the intersection 732 of the object 712 and the plane 724. During operation, a user may choose to rotate the cross-sectional plane (e.g., as shown by arrow 703 in FIGS. 7A and 7B) to transition, for example, from view 800*a* to view 900*a*. Both views (800*a*, 900*a*) show a plan view of a cross-sectional image and include needle 702 and a cross-sectional view of object 712. However, since the cross-sections for views 800*a* and 900*a* are taken at different planes (714, 724, respectively), the cross-sectional shape of the object 712 appears different between views 800*a* and 900*a*. In this example, object appears triangular in view 800*a*, but square in view 900*a*. Thus, changing between views vies 800*a* and 900*a* allows a user to view the object 712 within the volume from different perspectives while maintaining the needle 702 in the image in order to fully observe the location of the needle within the volume and with respect to the object.

As described, rotation of the cross-sectional plane (e.g., from plane 714 to plane 724) can occur about an axis in which the needle lies. For example, volumetric image data of a patient in which a needle is inserted can be processed in order to segment the needle within the volumetric image data and define a needle axis about which planar rotation can be performed. Rotation of the volumetric image data about the needle axis both increases the likelihood that the needle will be entirely or nearly entirely visible in the cross-sectional image and maintains the needle in approximately a fixed position during planar rotation. Such image processing and manipulation can make it easier for a user to identify where in a volume the needle is positioned and to understand and interpret the surroundings of the needle within the volume when compared to simply viewing parallel planar slices (e.g., from a stack of images) as in typical imaging systems.

As described with respect to FIGS. 1-3, in some examples, visualization system can be incorporated into a cryosurgery system, for example, wherein needle (e.g., 702) comprises a cryoneedle configured to freeze tissue to form an iceball within the patient, or when other ablation needles or probes are configured to ablate tissue by alternative ablation modalities. When used in real time during a cryosurgery procedure (e.g., during cryo or other ablation), the visualization system can be used to visualize the cross-sectional extent of a formed or forming iceball surrounding the needle in various directions or of the extent of ablated tissue, or the extent of a volume of tissue within which tissue death is predicted.

For example, with respect to cross-section at plane 724, views 900*a-c* include an exemplary iceball outline 750 within the image data. This may also represent the extent of ablated tissue, or the extent of a volume of tissue within which tissue death is predicted.

In cross-section at plane 724, the iceball 750 surrounds the object 712. Accordingly, if the object 712 were a lesion, the cross-sectional views 900*a-c* at plane 724 would indicate coverage of the lesion by the iceball 750. However, when rotated to show any of views 800*a-c* at plane 714, the iceball 750 does not surround the entire object 712 in plane 714. That is, due to different dimensions in different dimensions of the object 712 and/or the iceball 750, the iceball 750 may surround an object 712 in one plane (e.g., 724) but not another (e.g., 714). Accordingly, a user observing a real-time cryosurgery may advantageously rotate the cross-sectional plane through a plurality of views (e.g., 800*a-c*, 900*a-c*) in order to compare the dimension of an object 712 (e.g., a lesion) compared to the dimension of the iceball 750 in a plurality of dimensions. The user may then make an informed decision as to when a desired amount of the object 712 has been surrounded by the iceball 750, for example, to decide whether to end or continue the cryosurgery procedure.

The progress of ablation in other ablation modalities may be followed in the same manner, optionally in real time, by monitoring and displaying the volume of ablated tissue forming within the volume of patient tissue. The volume of ablated tissue may be followed in microwave or RF ablation, for example, by, e.g., ultrasound or thermography.

In some embodiments, the visualization system can be used to segment additional items within volumetric image data. For instance, in some embodiments, the visualization system can be used to segment an object, such as a lesion and/or an organ boundary within a patient's tissue (e.g., to identify voxels in the volumetric image data that correspond to the object). Additionally or alternatively, while shown in some examples as incorporating a single needle, various processes may involve placing a plurality of needles (e.g., cryoneedles, microwave or RF probes, ultrasound probes or electroporation probes) within the patient's tissue for adjusting the tissue impacted by various operations (e.g., the ablation procedure, e.g. cryoablation). The visualization system can be used to segment each of the plurality of needles or probes (e.g., automatically or via a manual selection). In some such examples, a user may select which of the plurality of needles is used to define the needle axis about which the volumetric image can be rotated to establish various cross-sectional views showing planes in which the selected needle approximately lies. Further, in some examples, a user can change which needle is selected in order to adjust the rotation axis and view additional cross-sectional images based on a needle axis defined by a subsequently selected needle from the plurality of needles.

Figure 10A:
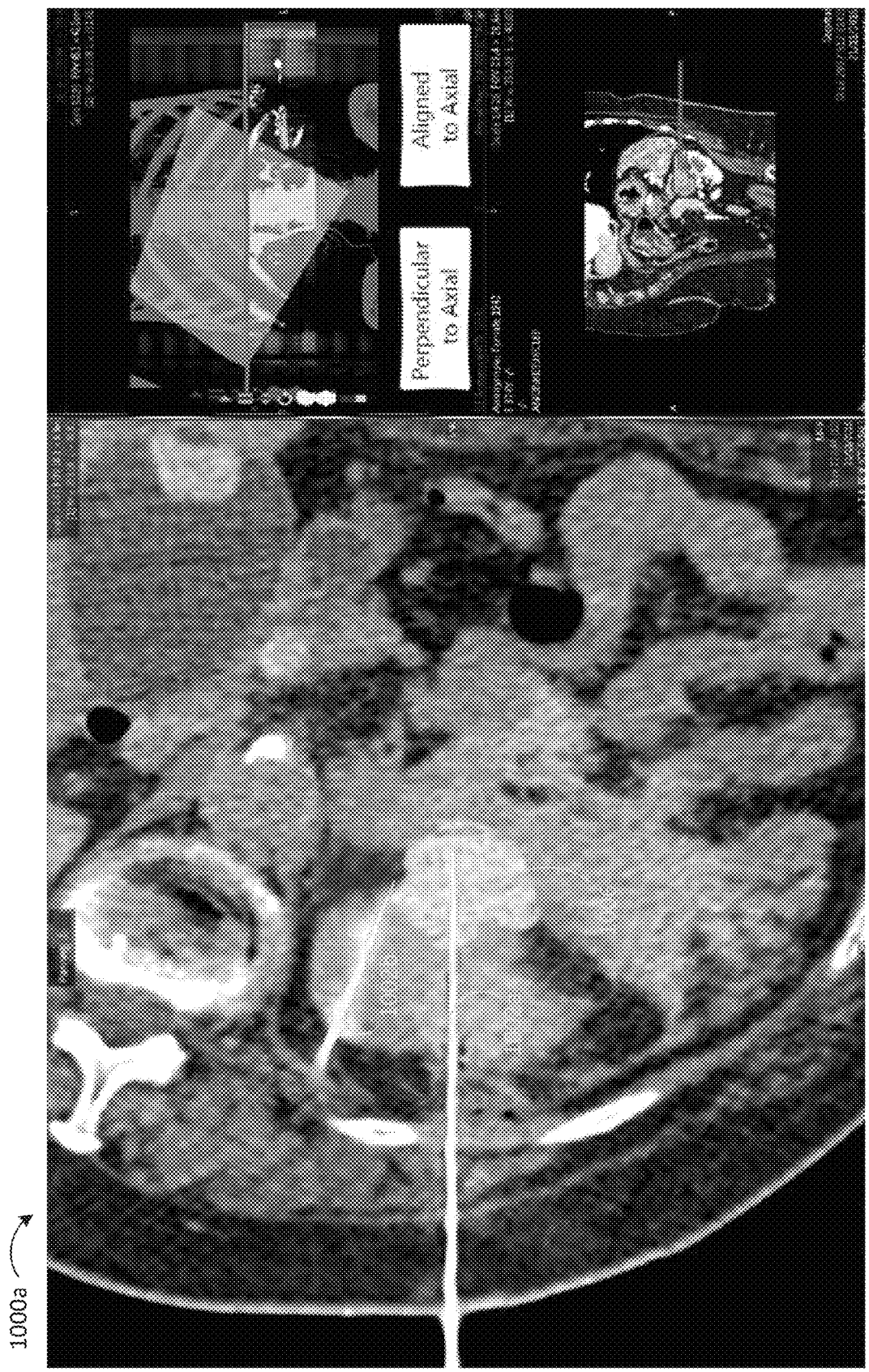
FIG. 10A shows an exemplary cross-sectional image of a volume of tissue including a pair of needles inserted therein.

FIG. 10A shows an exemplary cross-sectional image of a volume of tissue including a pair of needles inserted therein. The image 1000a of FIG. 10A shows a first needle 1002a, a second needle 1002b, and a lesion 1006 within the tissue. As discussed elsewhere herein, a visualization system can be configured to segment such structures within the tissue, for example, to identify which voxels in the volumetric image data and/or which pixels in cross-sectional image (e.g., 1000a) from the volumetric image data correspond to such structures.

Figure 10B:
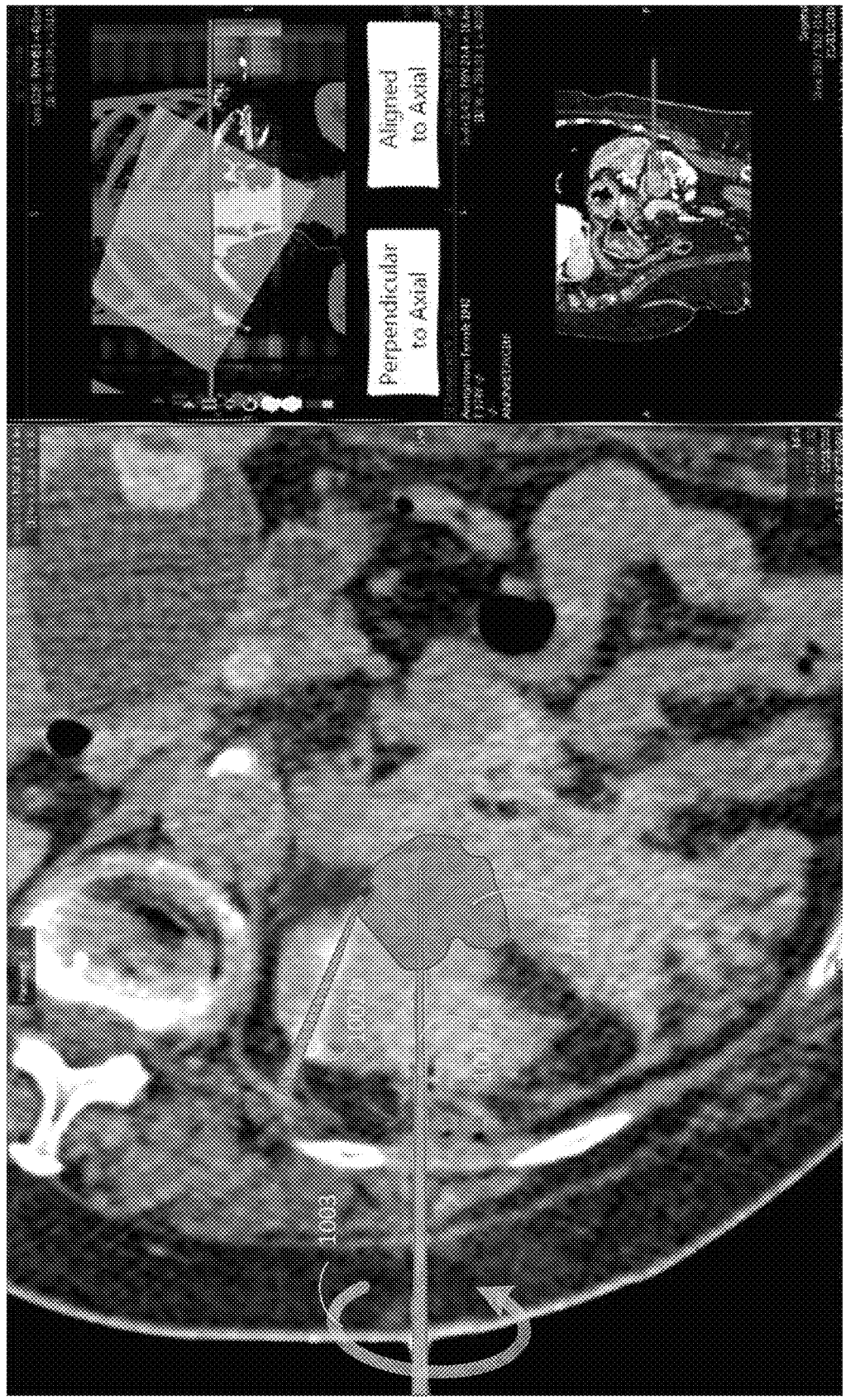
FIG. 10B shows the cross-sectional image of FIG. 10A with segmented portions of the image being emphasized.

FIG. 10B shows the cross-sectional image of FIG. 10A with segmented portions of the image being emphasized. For instance, FIG. 10B shows a cross-sectional image 1000b in which needles 1002a and 1002b, as well as lesion 1006, within the volume are segmented in the volumetric image data. In some embodiments, visualization system can display segmented objects in a contrasting display mode than other volumetric image data, such as in a contrasting color or the like. In the illustrated example, entire needle 1002a is visible within the cross-sectional image 1000b, while needle 1002b is only partially visible. This suggests that needle 1002b does not lie within the plane of the cross-sectional image 1000b, while needle 1002a does. Thus, according to some embodiments, needle 1002a defines a selected (e.g., automatically or manually) needle axis used to select a cross-sectional plane for generating cross-sectional image 1000b. As described elsewhere herein, a user may rotate the volumetric image data about the needle axis, for example, as shown by arrow 1003, in order to select additional or alternative planes for which to generate cross-sectional image data.

Figure 10C:
FIG. 10C shows the cross-sectional view of FIG. 10B including additional segmented objects, such as an iceball.

Other objects that may be segmented within volumetric image data include an iceball that has formed and/or is forming within the tissue, or a developing volume of ablated tissue, or a volume of tissue within which tissue death is predicted, brought about by any modality FIG. 10C shows the cross-sectional view of FIG. 10B including additional segmented objects, such as an iceball, but this may equally be a volume of ablated tissue, or a volume of tissue within which tissue death is predicted, for example based on the actual or predicted temperature or on a model. In the example of FIG. 10C, treatment region 1050, for example, formed by needles 1002a, 1002b, is shown being formed within the cross-sectional image 1000c. In some embodiments, visualization system can be configured to identify the treatment region 1050 within the volume, and present the treatment region 1050 in a contrasting color in a cross-sectional image (e.g., 1000c).

In some embodiments, the presentation of treatment 1050 can include a plurality of regions (e.g., 1052, 1054), which can be used to indicate additional information to a user. For instance, in some embodiments, the treatment region can include a segmented iceball, or segmented volume of ablated tissue, or a segmented volume of tissue within which tissue death is predicted, 1054 and the outline of a margin 1052 surrounding the iceball or tissue volume 1054. In various examples, the identified margin 1052 can be positioned a fixed distance surrounding the perimeter of the iceball or volume of ablated tissue, or volume of tissue within which tissue death is predicted, 1054. For example, in some such embodiments, the visualization system can be configured to identify physical dimension within the volumetric image and measure a predetermined distance from the perimeter of the segmented iceball, or segmented tissue volume, 1054 for determining the margin 1052. In some embodiments, the margin 1052 distance from the iceball, or tissue volume 1054 perimeter can be adjusted by a user, for example, via a user interface.

Additionally or alternatively, as mentioned elsewhere herein, systems can include one or more temperature sensors positioned in or proximate a needle, or probe (e.g., a cryoneedle) that can provide temperature information representative of the temperature of tissue proximate the needle. Accordingly, in some embodiments, treatment region 1050 can include one or more isotherms or other temperature representations identifying the temperature within the volume. In an exemplary embodiment, iceball 1054 can represent volumetric regions that are at or below −10° C., while margin 1052 can represent volumetric regions that are between −10° C. and 0° C. In modalities where the temperature is raised to bring about the ablation, isotherms may represent the borders of tissue volumes within which tissue death is predicted, whilst a margin can represent temperatures where complete ablation or death is not expected, or may be of a lower probability. In some approaches, the isotherms may represent the borders of regions having a probability of tissue death, for example 75%, 80% 90% or 100% probability of tissue death. within these isotherms there may therefore be a probability of between 75% and 80% of tissue death 80-90% or 90-100%. In general, a processing system (e.g., visualization system and/or control system) can be configured to receive and/or determine volumetric temperature information in order to establish temperature data for a plurality of voxels (e.g., voxels proximate the needles 1002a, 1002b) in order to visually represent temperature values and/or ranges in the cross-sectional image (e.g., 1000c). In some embodiments, the temperature values and/or ranges to be displayed by visualization system and/or the contrasting color scheme in which such temperature information is displayed can be selectable by a user. For instance, in an exemplary embodiment, a user may wish to view a variety of isotherms representing temperature values within the tissue, which may or may not include a literal iceball, a volume of ablated tissue, or volume of tissue within which tissue death is predicted. In another example, the visualization system may segment the iceball or tissue volumes and display the iceball, or tissue volumes in one color scheme (e.g., in a particular contrasting color) and may further present selected temperature values (e.g., isotherms) in a separate color scheme. In various examples, convenient isotherms can include one or more of 60° C. (e.g., in a thermal ablation treatment system), 0° C., −20° C., and/or −40° C. In some examples, the isotherm may represent the extent of a volume within which tissue death is predicted, for example based on models e.g. of given tissue survival at a particular temperature/time. This may be cryoablative or may be a system such as microwave or RF, for example In some embodiments, the processing system can receive temperature values from one or more temperature probes inserted into the visualized tissue (e.g., on or near needles 1002a, 1002b) in order to determine temperature data representative of temperature values in the volume. In some such examples, the processing system can be configured to use temperature values received from such probes that indicate temperature values at one or more locations and calculate expected temperature values for regions proximate those for which the temperature is measured. Such calculated temperatures can be based on, for example, volumetric tissue data that can be used to estimate the thermal behavior of the tissue at locations at which temperature probes are not positioned.

Additionally or alternatively, temperature data for a plurality of voxels in the volumetric image data can be calculated without using temperature probes to physically measure temperature. In some embodiments, operating data of one or more surgical tools, for example, power data representative of the electrical power consumed by one or more cryoneedles, can be used to determine approximate temperature values proximate the surgical tool(s). Further, in some examples, volumetric image data can be used in combination with such operating data to predict the thermal behavior of the surrounding tissue to estimate the temperature profile of the volume.

In some embodiments, visualization system can be configured to analyze various segmented regions within the volumetric image data to determine overlap of such regions. For example, with respect to FIG. 10C, the lesion 1006 as displayed in FIG. 10B is broken down into three regions—a first region 1016, a second region 1026, and a third region 1036—based on the overlap of lesion 1006 and portions of treatment region 1050. In the illustrated example, the first region 1016 of lesion 1006 does not overlap with identified treatment region 1050, the second region 1026 of lesion 1006 overlaps with the margin 1052 section of the treatment region 1050, and the third region 1036 of lesion 1006 overlaps with the iceball 1054 section of treatment region 1050. As indicated in the example of FIG. 10C, such regions (1016, 1026, 1036) of lesion 1006 can be visually distinct in cross-sectional image 1000c so that a user may quickly and easily identify the volumetric extent of the treatment (e.g., treatment volume 1050) with respect to the segmented lesion 1006). For example, a user may be able to quickly visualize whether or not an iceball, volume of ablated tissue, or volume of tissue within which tissue death is predicted (e.g., 1054) has sufficiently surrounded the lesion 1006.

As described elsewhere herein, for example, with respect to FIGS. 7A-7B, 8A-8C, and 9A-9C, in various embodiments, the visualization system may be configured to facilitate rotation of the cross-sectional plane about an axis (e.g., a needle axis). For example, FIGS. 10A-10C show a cross-sectional image (1000a-1000c) in which a needle 1002a lies. As shown in FIGS. 10B-10C, visualization system can segment the needle 1002a within the volumetric image data, and can establish a cross-sectional image 1000a-1000c showing a plane in which the needle lies. As described elsewhere herein, the view can be rotated to one or more additional planes in which the needle lies, for example, by rotating the volumetric image about the needle 1002a while maintaining the location of the needle 1002a in the same location. That is, in some embodiments, as the volumetric image data is rotated about the needle axis (e.g., from a first cross-sectional view to a second cross-sectional view), the pixel coordinates of the needle in the first and second cross-sectional views are approximately the same.

Rotating the view of the cross-sectional image allows a user to view the various information displayed, for example, in FIG. 10C, from a plurality of perspectives. For example, rotating the view according to arrow 1003, a user could view the overlap of treatment region 1050 and lesion 1006 in a plurality of planes and from a plurality of perspectives. This can allow for a more complete determination of the extent of the treatment volume 1050 with respect to that of the lesion 1006. For instance, with respect to the simplified example in FIGS. 8A-8C and 9A-9C, in some views (e.g., 900a-900c), the iceball 750 surrounds the entire outline 732 of object 712. However, in other views (e.g., 800a-800c), the iceball 750 does not surround the entire outline 722 of object 712. Thus, different perspectives can provide more thorough information representing the relationship between a treatment region 1050 and a lesion 1006.

This can help increase the likelihood that an entire lesion 1006 receives appropriate treatment in all directions, and reduces the likelihood of insufficient treatment based on only a singular view or a small plurality of parallel views. Similarly, viewing such volumes in a variety of planes enables a user to view the location of a treatment volume 1050 (e.g., a margin 1052 surrounding an iceball, volume of ablated tissue, or volume of tissue within which tissue death is predicted 1054) with respect to other anatomical features of a patient. For instance, in one example, a user may observe a growing treatment volume (e.g., during application of a treatment) and choose to stop or adjust the treatment procedure if the treatment volume comes too close (e.g., within an iceball, or tissue volume margin 1052) of an anatomical structure of a patient that may be undesirably impacted by the treatment, such as an organ boundary.

Figure 11:
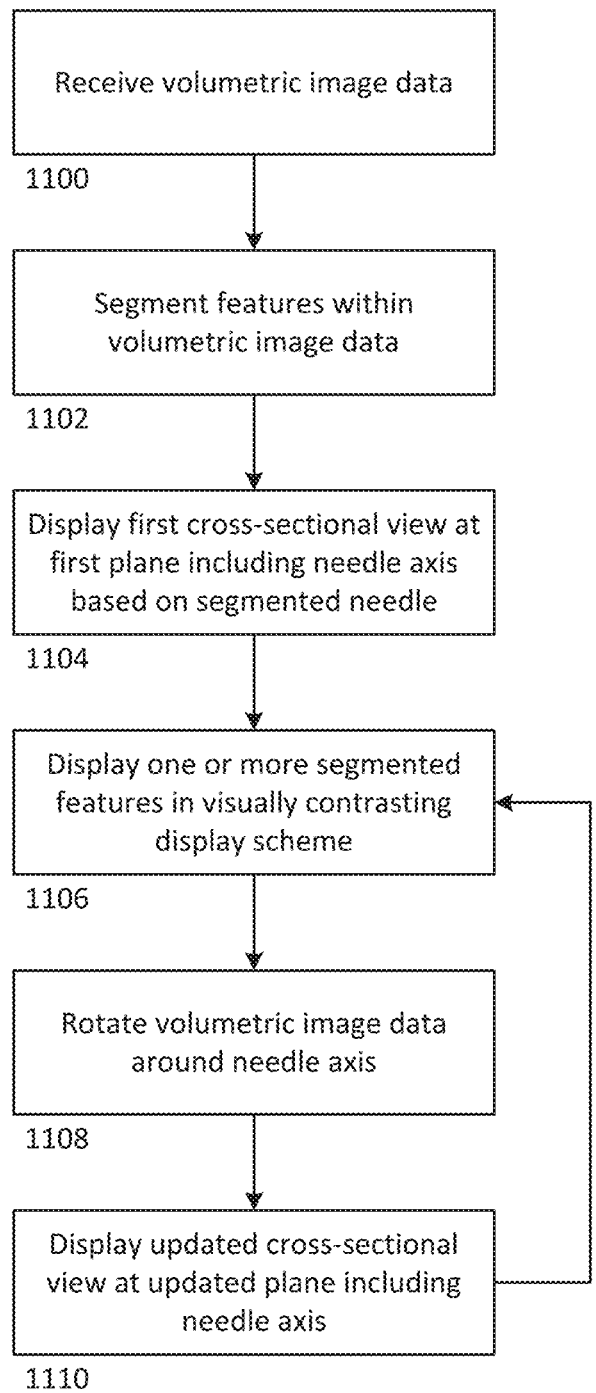
FIG. 11 is a process-flow diagram showing exemplary process for displaying volumetric image data.

FIG. 11 is a process-flow diagram showing exemplary process for displaying volumetric image data. The method of FIG. 11 includes receiving volumetric image data (1100) representing a volume, for example, from a volumetric image scanner (e.g. a CT scanning system). The volumetric image data can be segmented (1102) to determine the volumetric location (e.g., voxel coordinates) corresponding to different structures in the volume. A visualization system can be configured to display a first cross-sectional view (1104), which can be show a first plane that includes a needle axis based on a segmented needle (e.g., from step 1102). The visualization system can be further configured to display one or more segmented features on a display in a contrasting display scheme (1106). For example, segmented needle(s), lesion(s), organ(s), etc. can be displayed in one or more colors that contrast with the display scheme of the traditional volumetric image data, such as colorized segmented objects in a black-and-white or grayscale cross-sectional image. Additionally or alternatively, a contrasting display scheme can include flashing boundaries/areas, emphasized outlines, or the like.

The method further includes the step of rotating the volumetric image data around the needle axis (1108), and displaying an updated cross-sectional view showing an updated plane that includes the needle axis (1110). For example, with respect to FIGS. 7A and 7B, the visualization system can rotate a first cross-sectional view showing a first plane 714 to an updated cross-sectional view showing an updated plane 724, for example, by rotating the volumetric image data around axis 701. After rotating to the updated cross-sectional view, the one or more segmented features can be displayed in a visually contrasting display scheme (1106), as described elsewhere herein. In various examples, the steps of rotating the volumetric image data (1108) and displaying an updated cross-sectional view (1110) can be performed as many times as desired, for example, as a user analyzes volumetric image data from a plurality of perspectives.

In various examples, some steps of the method shown in FIG. 11 can be performed manually by a user, automatically by a processing system or can be divided between a user and a processing system. For example, in some embodiments, a processing system (e.g., via a visualization system) can automatically receive volumetric image data, for example, from a volumetric image scanner, for analysis. In other examples, a user may manually upload volumetric image data into a processing system for analysis. In some examples, segmentation of volumetric image data can be performed automatically, or may be based on one or more manual inputs. For instance, in some examples, a user may apply a label (e.g., "lesion") to an automatically-segmented volume to assist in a segmentation process. In various examples, rotating the volumetric image data about a needle axis (1108) can be performed manually, for example, by a user rotating the view via a user interface. Additionally or alternatively, a processing system (e.g., a via a visualization system) can be configured to automatically rotate the volumetric image data about the axis, for example, at a programmable rotational speed (e.g., in degrees/second).

In some such embodiments, segmented volumetric image data and associated analysis, for example, as shown in and discussed with respect to FIG. 10C, can be used to control operation of one or more surgical tools. In an exemplary embodiment, the processing system (e.g., via a visualization system) can be configured to segment items in the volumetric image data in approximately real time during an operation, such as during a cryosurgery operation. The processing system can be configured to automatically compare one or more operation results (e.g., an iceball size, volume of ablated tissue, or volume of tissue within which tissue death is predicted, or one or more isotherms, etc.) to the size of a segmented lesion within the volumetric image data. In some such examples, the processing system (e.g., via a control system) can be configured to automatically stop the surgical operation (e.g., to stop cryo or other ablation) when a treatment volume (e.g., an iceball, ablated tissue or predicted tissue death volume, an iceball, or respective tissue margin volumes, etc.) reaches a predetermined size with respect to the size of the lesion.

For instance, in an exemplary embodiment, the treatment can be automatically stopped when the iceball, volume of ablated tissue or volume of tissue within which tissue death is predicted reaches a predetermined size relative to the segmented lesion, such as when the volumetric boundary of the iceball or tissue volume surrounds the entirety of the volumetric boundary of the lesion. In various examples, the processing system can be programmed with instructions for performing one or more analyses that can be used to initiate various system operations, such as determining when a treatment process should be stopped. In some such examples, such instructions can be based on instructions programmed by a user, for example, via a user interface. For instance, in an exemplary embodiment, a user may define a relationship between an iceball, ablated tissue, or predicted tissue death volume and a lesion volume that, when reached, will cause the system to stop the ablation (e.g. cryoablation), (e.g., via control system 40). Additionally or alternatively, a user may define a relationship between an iceball ablated tissue volume, or predicted tissue death volume boundary or margin and an organ boundary that, when met, causes the system to stop an ablation (e.g. cryoablation) process (e.g., via control system 40).

Figure 12:
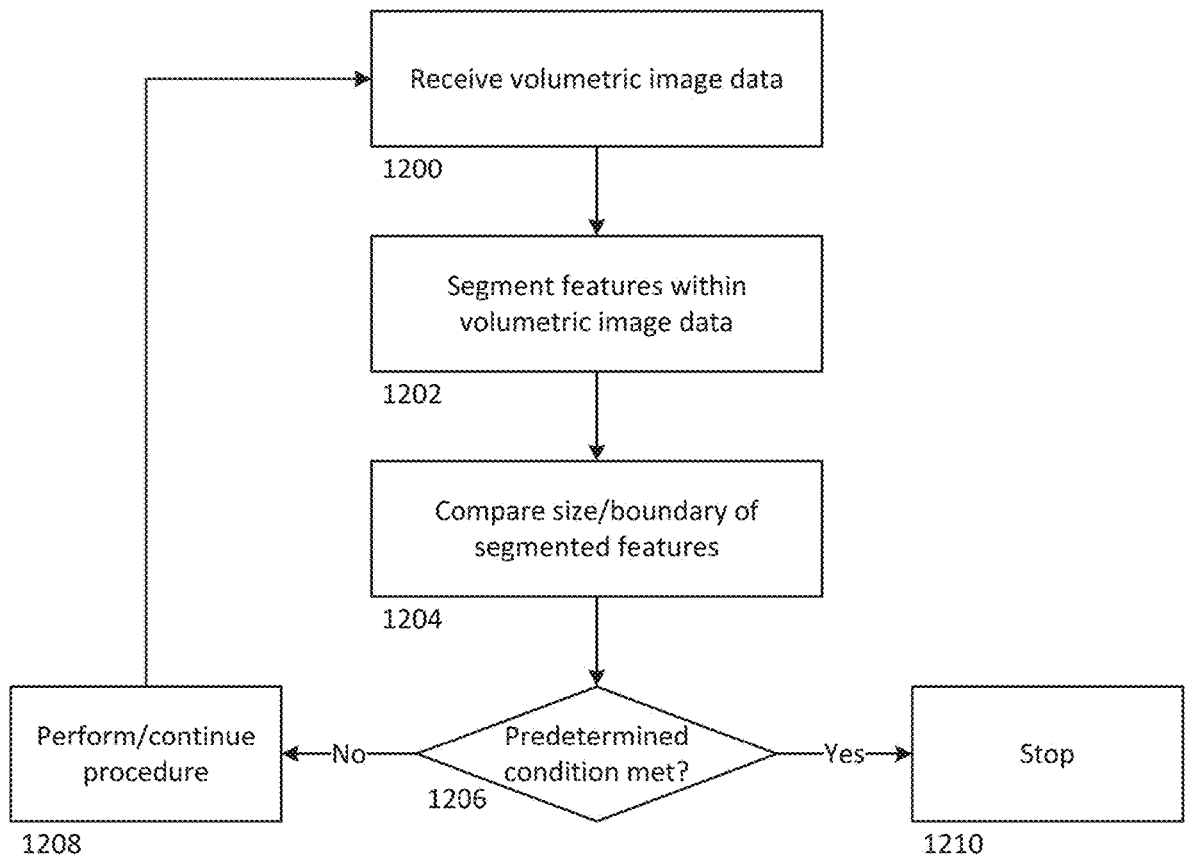
FIG. 12 is a process-flow diagram illustrating an exemplary control method for controlling a procedure based on volumetric image data analysis.

FIG. 12 is a process-flow diagram illustrating an exemplary control method for controlling a procedure based on volumetric image data analysis. The method includes the steps of receiving volumetric image data (1200) and segmenting features within the volumetric image data (1202), for example, one or more treatment volumes, lesions, organs, or the like. The method can include the steps of comparing the size and/or boundary locations of one or more segmented features (1204), and determining, for example, based on the comparison, if one or more predetermined conditions are met (1206). If not, a procedure can be performed (e.g., if the procedure had not yet started) or continued (e.g., if condition is determined during a procedure) (1208), and the process can be repeated. However, if the predetermined condition is met (e.g., at 1206), a procedure (e.g., a surgical procedure) can be stopped.

In various examples, such predetermined conditions can relate to relative sizes and/or boundary locations of one or more segmented features relative to others. In an exemplary embodiment, determining whether or not a predetermined condition is met comprises determining whether or not the boundary of an iceball, ablated tissue volume or predicted tissue death volume completely overlaps the boundary of a lesion. Additionally or alternatively, determining whether or not a predetermined condition is met comprises determining whether or not a margin surrounding the iceball, ablated tissue volume or predicted tissue death volume overlaps a boundary of a patient organ. In general, one or more predetermined conditions can be implemented in order to ensure that, for instance, during a surgical procedure (e.g., cryosurgery), sufficient treatment is performed and no undesired harm is done. In some examples, predetermined conditions can include a plurality of conditions, such as one or more Boolean combinations of different conditions (e.g., condition A and condition B). In some embodiments, a plurality of predetermined conditions can be saved in memory and/or can be customized by a user.

In various embodiments, certain steps in the method of FIG. 12 can be performed automatically by a system (e.g., via a processing system), manually by a user, or by a combination of the system and a user. For example, as described elsewhere herein, in some embodiments, a visualization system can receive volumetric image data automatically (e.g., from a volumetric image scanner) and/or can receive volumetric image data via manual upload. Further, a system may be capable of automatically segmenting features within volumetric image data, or may do so with input from a user as described elsewhere herein.

In some embodiments, a processing system may be configured to automatically detect if a predetermined condition is met, such as if an iceball, ablated tissue volume or predicted tissue death volume boundary surrounds a lesion boundary. In other examples, the processing system may display a segmented iceball, ablated tissue volume or predicted tissue death volume and a segment lesion in one or more cross-sectional views as described elsewhere herein in order for a user to identify whether or not a predetermined condition is met based on the visualized volumetric image data. If a user identifies whether or not a predetermined condition is met, the user can initiate a procedure, allow a procedure to continue, or stop a procedure. If the processing system identifies one or more predetermined conditions is met, the processing system can initiate a procedure, allow a procedure to continue, stop a procedure, or alert a user of the predetermined condition so that the user may take appropriate action(s). Alerting the user can include notifying the user of the predetermined condition, for example, via visual alert, audio alert, or the like. The processing system may present the user with an alert of the satisfied or unsatisfied predetermined condition and/or may present the user with one or more suggested actions in view of the met or unmet condition.

In various examples, such processes can be used to analyze and/or simulate needle placement within any volume of a patient's tissue. Additionally, while several features have been described herein with respect to segmenting volumetric image data including a needle inserted into tissue of a patient, similar techniques can be used in other areas, such as endoscopic processes in which CT or MRI imagery is used to assist in guiding an instrument within a patient. Additionally or alternatively, in some examples, systems can perform techniques similar to those described herein in order to plan a treatment for a patient (ablation e.g., a cryoablation procedure).

Figure 13A:
FIG. 13A shows a cross-sectional view of exemplary volumetric image data, for example, obtained from a volumetric image scanner.
Figure 13B:
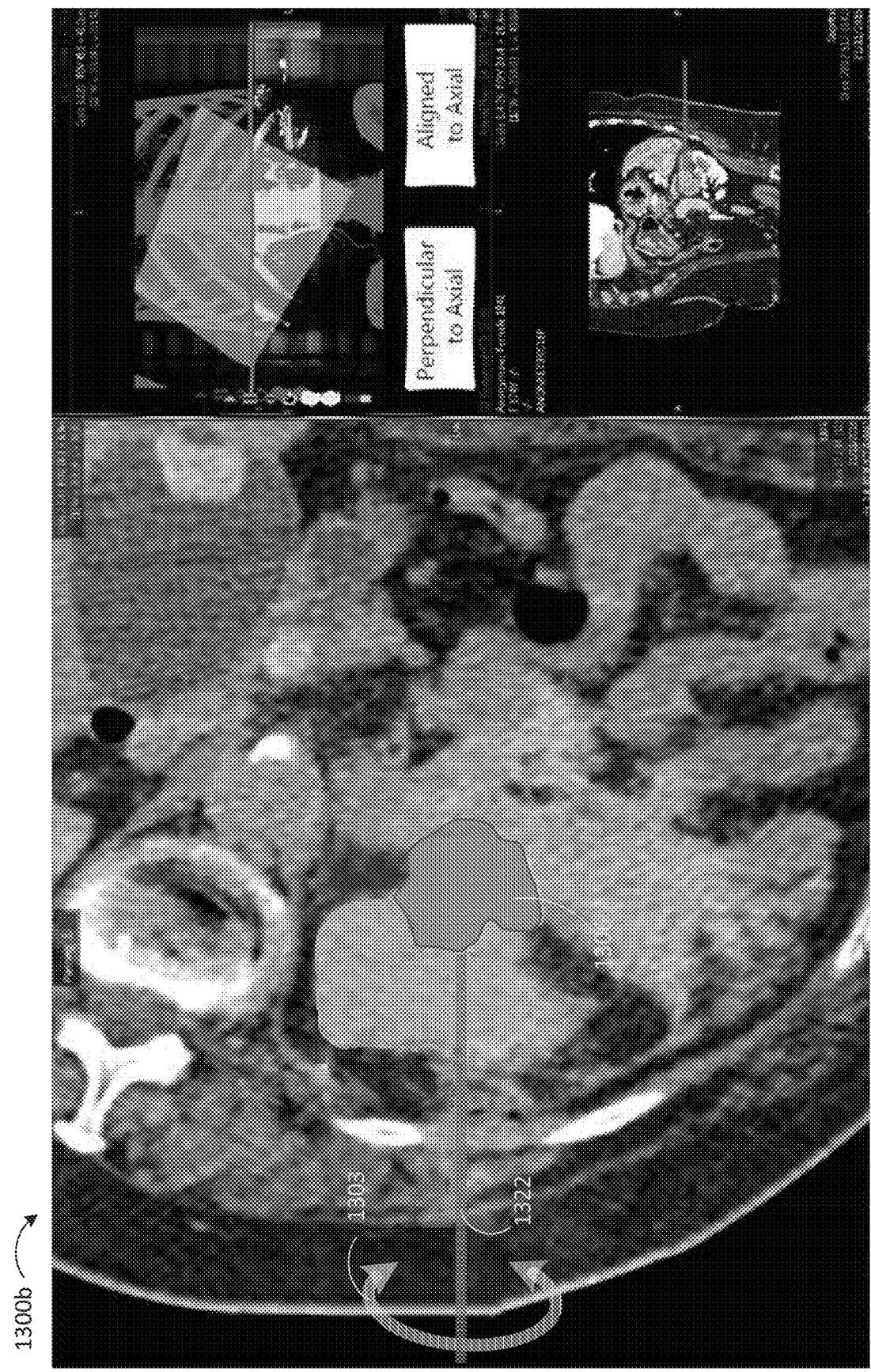
FIG. 13B shows a cross-sectional view of segmented volumetric image data.

FIG. 13A shows a cross-sectional view of exemplary volumetric image data, for example, obtained from a volumetric image scanner. As described elsewhere herein, in some embodiments, a processing system (e.g., via a visualization system) can be used to segment the volumetric image data. FIG. 13B shows a cross-sectional view of segmented volumetric image data. The cross-sectional view of FIG. 13B 1300b includes a segmented lesion 1306. The segmented objects (e.g., lesion 1306) can be displayed in a contrasting display scheme from the other volumetric image data. In some embodiments, a visualization system can be configured to position a virtual needle 1322 within the volumetric image data. Virtual needle 1322 can be positioned manually by a user or can be positioned automatically, for example, at a system-recommended location. In some examples, a user may adjust the position of the virtual needle 1322 within the volumetric image data in real time.

Similar to processes discussed elsewhere herein with respect to a segmented needle/probe (e.g., cryoneedle), the virtual needle 1322 can define a virtual needle axis extending through the volumetric image data. Cross-sectional image 1300b in FIG. 13B can be taken at a plane in which the virtual needle axis defined by virtual needle 1322 lies. In some examples, the volumetric image data can be rotated about the virtual needle axis as indicated by arrow 1303, similar to processes described elsewhere herein. This can allow for different cross-sectional views of the volumetric image data, including lesion 1306.

In some embodiments, a processing system can be further configured to simulate a treatment (ablation e.g., a cryoablation) and display the result of the simulated treatment. For example, with respect to a cryo, or other ablation process, the processing system (e.g., via a visualization system) can be configured to, based on the location of the virtual needle, simulate the development of an iceball, ablated tissue volume or predicted tissue death volume and/or a temperature progression of the volume proximate the virtual needle 1322. In some examples, such simulated treatment results can be based on one or more additional input parameters, such as in input power, a treatment duration, an input power vs. time curve, or the like.

Figure 13C:
FIG. 13C is an exemplary cross-sectional image showing a virtual needle and the result of a simulated treatment procedure.

FIG. 13C is an exemplary cross-sectional image showing a virtual needle and the result of a simulated treatment procedure. In the illustrated example, virtual needle 1322 is positioned within the volumetric image data of a patient's tissue proximate a segmented lesion 1306. As shown, a virtual treatment region 1350 is shown proximate the virtual needle 1322. As discussed, the virtual treatment region 1350 may be a function of a plurality of inputs, such as a needle position, needle operating power, operating time, etc.

Virtual treatment region 1350 includes a first region 1352 and a second treatment region 1354. In some examples, the first region 1352 can correspond to a virtual margin surrounding a virtual iceball, or virtual ablated tissue volume represented by the second region 1354. Additionally or alternatively, regions 1352, 1354 can represent virtual isotherms and/or temperature ranges within the volume.

Similar to as described with respect to FIG. 10C, the visualization system can be configured to analyze the locations of the virtual treatment region(s) (e.g., iceball, virtual tissue ablation volume, margin, etc.) with respect to the location of segmented objects in the actual volumetric image data (e.g., a lesion, an organ boundary, etc.). The visualization system can be configured to identify overlap between such regions, and visually indicate the portions of such segmented features that overlap with the virtual treatment volume.

In the example of FIG. 13C, the lesion 1306 is shown having three regions. A first region 1316 does not overlap any of the treatment region, a second region 1326 overlaps the first region 1352 of the treatment volume 1350, and a third region 1336 overlaps the second region of the treatment volume 1350. Thus, the impact of the simulated treatment on the lesion 1306 can be readily observed by a user viewing the results of the simulation. Moreover, as the virtual treatment is performed on the volumetric image data, the cross-sectional view may be rotated about an axis (e.g., a virtual needle axis defined by virtual needle 1302), for example, as indicated by arrow 1303. As described elsewhere herein, this allows for visualization of the cross-sectional extents of various features (e.g., lesion 1306, virtual treatment region 1350) in a plurality of planes, each of which contains the virtual needle 1322.

A user may adjust the one or more virtual treatment parameters to visualize the impact on such adjustments, such as for applying a treatment (e.g., a cryo or other ablation procedure) for a different period of time and/or with a different amount of applied power, frequency etc. Additionally, while shown with a single virtual needle 1322, it will be appreciated that a plurality of virtual needles may be inserted into the volume in order to impact the virtual treatment. FIGS. 14A-C shows exemplary iceball formation and thermal gradients for a plurality of needle configurations, but this example is equally applicable to the formation of a volume of ablated tissue, or a volume of predicted tissue death FIG. 14A shows an iceball 1450 formed by a single needle 1402. In the example of FIG. 14A, an iceball 1450 grows approximately symmetrically about the needle. Iceball 1450 include three regions, 1452, 1454, 1456, which can, for example, correspond to different temperature ranges. In an exemplary embodiment, region 1452 corresponds to temperatures between −20° C. and 0° C., region 1454 corresponds to temperatures between −40 and −20° C., and region 1456 corresponds to temperatures below −40° C.

FIG. 14B shows an iceball 1460 formed by a pair of cryo needles 1412a, 1412b. Similar to the iceball 1450 of FIG. 14A, iceball 1460 include three regions, 1462, 1464, 1466, which can, for example, correspond to different temperature ranges. In an exemplary embodiment, region 1462 corresponds to temperatures between −20° C. and 0° C., region 1464 corresponds to temperatures between −40 and −20° C., and region 1466 corresponds to temperatures below −40° C. However, the cross-section of iceball 1460 of FIG. 14B and regions 1462, 1464, 1466 are shaped differently than iceball 1450 and regions 1452, 1454, 1456 due to the presence of two needles (1412a, 1412b) contributing to iceball formation rather than one (1402).

FIG. 14C shows an iceball 1470 formed by three cryo needles 1422a, 1422b, 1422c. Similar to the iceball 1450 of FIG. 14A, iceball 1470 include three regions, 1472, 1474, 1476, which can, for example, correspond to different temperature ranges. In an exemplary embodiment, region 1472 corresponds to temperatures between −20° C. and 0° C., region 1474 corresponds to temperatures between −40 and −20° C., and region 1476 corresponds to temperatures below −40° C. However, the cross-section of iceball 1470 of FIG. 14B and regions 1472, 1474, 1476 are shaped differently than iceball 1450 and regions 1452, 1454, 1456 due to the presence of three needles (1422a, 1422b, 1422c) contributing to iceball formation rather than one (1402).

As shown by the different iceball shapes/temperature distributions in FIGS. 14A-14C, adjusting the number and/or location of treatment needles (e.g., cryoneedles) can impact the volume impacted by treatment. Thus, in some examples, in performing a virtual treatment as described with respect to FIG. 13C, a user (or a system configured to recommend a particular treatment) may place a plurality of virtual needles in the volumetric tissue data in order to simulate a treatment plan for any ablation modality.

Figure 15:
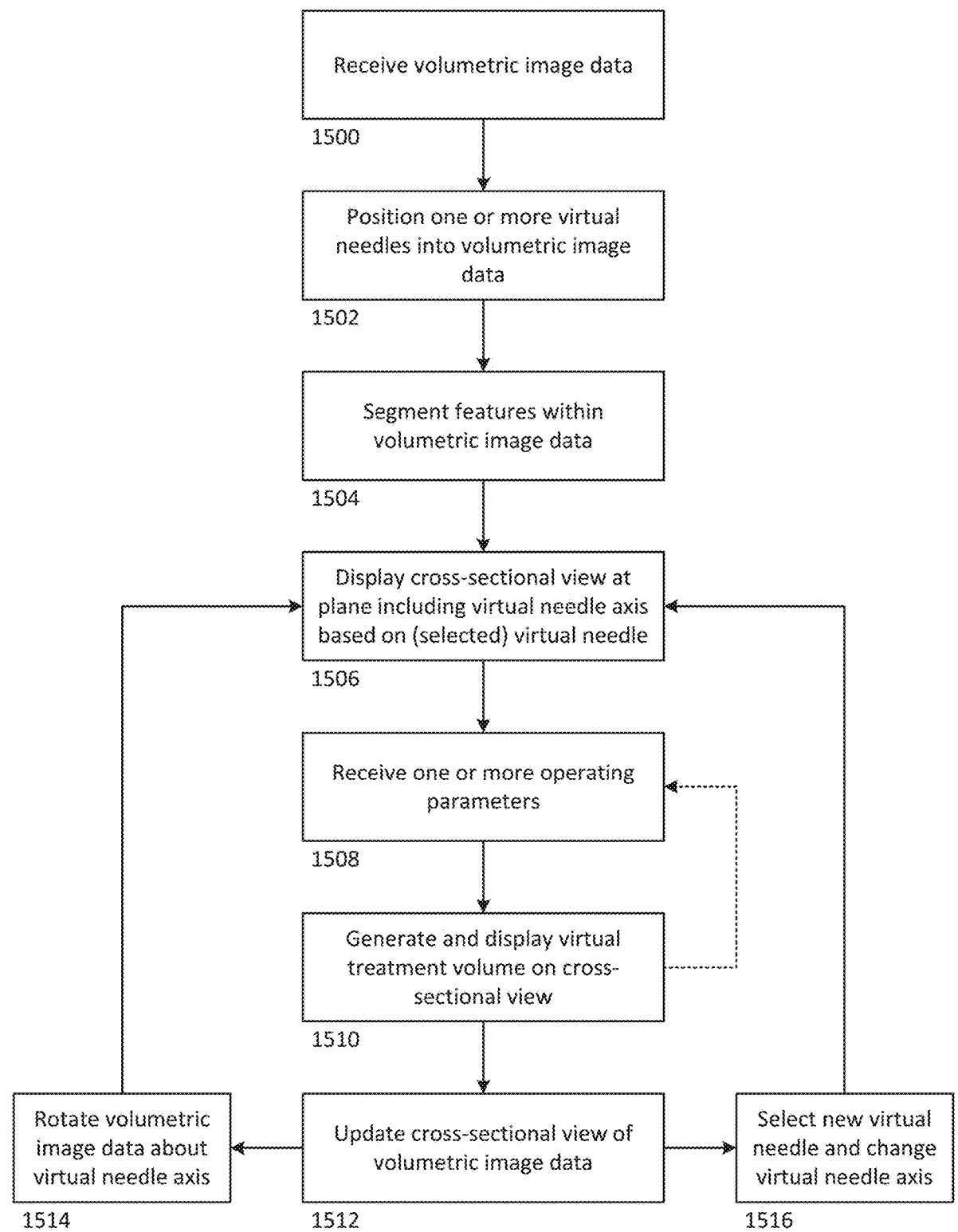
FIG. 15 is a process flow diagram illustrating an exemplary process for generating and displaying a simulated treatment plan.

FIG. 15 is a process flow diagram illustrating an exemplary process for generating and displaying a simulated treatment plan. The method of FIG. 15 includes receiving volumetric image data (1500), for example, from a volumetric image scanner, or from a memory in which the image data has been stored. The method includes the step of positioning one or more virtual needles into the volumetric image data (1502) and segmenting features within the volumetric image data (1504).

The method includes displaying a cross-sectional view at a plane including a virtual needle axis based on a virtual needle (1506). In some instances, for example, in the case of a plurality of virtual needles inserted in step 1502, the needle axis could be based on a selected one of a plurality of virtual needles. The method includes the steps of receiving one or more operating parameters (1508), for example, operating parameters of a treatment, such as an operating power or frequency or treatment duration, and generating and displaying a treatment volume on the cross-sectional view (1510). In some examples, the generated treatment volume can be based on the received one or more operating parameters. Such a virtual treatment volume can be used to determine whether or not the simulated treatment (e.g., based on one or more received parameters from stop 1506) has the desired impact on the volume, such as whether or not a particular section of the treatment volume fully overlaps a segmented lesion.

In various examples, the cross-sectional view including the generated virtual treatment volume can be created so that various portions are displayed in a contrasting display scheme, such as contrasting colors of the like. For example, one or more segmented features, such as a lesion, an organ boundary, or the like, as well as a virtual treatment volume, can be displayed in one or more contrasting colors from the other volumetric image data shown in the cross-sectional view. Additionally or alternatively, areas of overlap between one or more such regions can be displayed in a contrasting display scheme, for example, as shown in FIG. 13C. In some embodiments, a user may manually select which features are displayed in a contrasting display scheme, and in some such examples, can select how one or more of such features are displayed.

In some embodiments, after displaying a virtual treatment volume, the method can include receiving one or more operating parameters (1508), for example, to update the virtual treatment volume. For instance, in an exemplary embodiment, a user may view the virtual treatment volume along with a segmented lesion and/or organ boundary, and may wish to adjust one or more of the operating parameters that contribute to the virtual treatment volume. Such parameter adjustment(s) can be used to fine-tune the virtual treatment in order to achieve the desired treatment volume, and in some examples, treatment volume characteristics (e.g., isotherms, etc.)

The method of FIG. 15 further includes the step of updating the cross-sectional view of the volumetric image data (1512). In some examples, updating the cross-sectional view comprises rotating volumetric image data about the virtual needle axis (1514), such as described elsewhere herein. Additionally or alternatively, in processes in which a plurality of virtual needles are inserted into the volume, updating the cross-sectional view (1512) can include selecting a new virtual needle and changing the virtual needle axis (1516) that in included in the cross-sectional plane. In either case, after updating the cross-sectional view, the method can revert to the step of displaying a cross-sectional view at a plane that includes the virtual needle axis based on the selected (and possibly updated) virtual needle.

It will be appreciated that, in various embodiments, steps of the exemplary method of FIG. 15 may be omitted or permuted, and additional steps may be included. For instance, in another exemplary embodiment, the steps of positioning one or more virtual needles into the volumetric image data (1502) and segmenting features within the volumetric image data (1504) may be permuted, wherein features (e.g., one or more lesions, organ boundaries, etc.) are segmented prior to positioning one or more virtual needles. Processes can include a step of adjusting the positioning and/or the number of virtual needles within the volumetric image data.

In addition to treatment planning processes, for example, visualizing virtual needles and virtual treatment volumes in volumetric image data of a real environment, and treatment monitoring processes, for example, visualizing real needles and real treatment volumes in volumetric image data, in some examples, combinations of such processes can be performed. For example, in some embodiments, systems can be configured to use segmented real needles in volumetric image data in order to generate a virtual treatment volume based on a likely progression of a treatment process given the position of the needle(s) in the volume.

Figure 16:
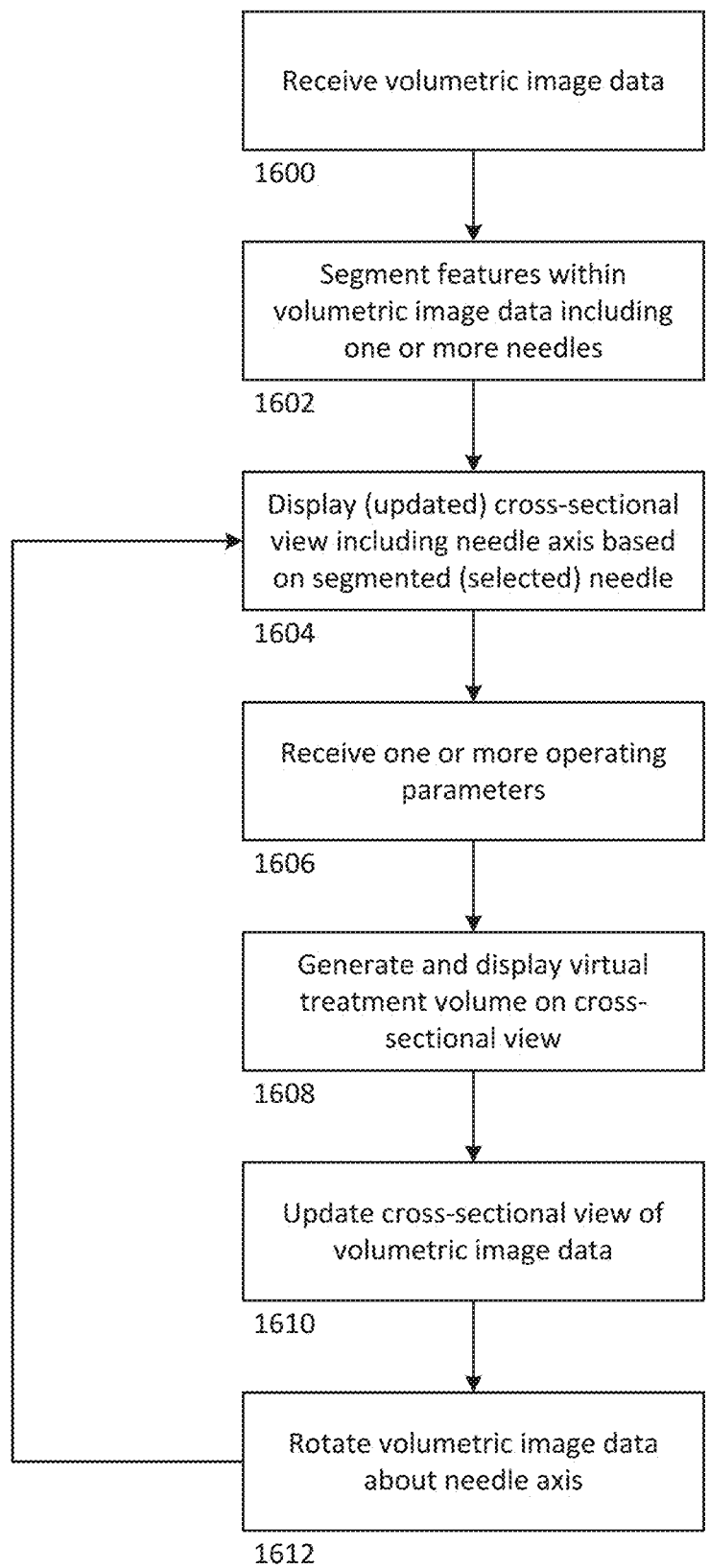
FIG. 16 is a process-flow diagram showing an exemplary method for generating virtual treatment volumes using segmented needles in volumetric image data.

FIG. 16 is a process-flow diagram showing an exemplary method for generating virtual treatment volumes using segmented needles in volumetric image data. The method includes receiving volumetric image data (1600) and segmenting features within the volumetric image data including one or more needles (1602). The method further includes displaying a first cross-sectional view including a needle axis based on one (e.g., a selected one) of the one or more segmented needles (1604), such as described elsewhere herein.

The method includes the steps of receiving one or more operating parameters (1606), such as, for example, operating power, operating time, or the like, and generating and displaying a virtual treatment volume on the cross-sectional view (1608). The virtual treatment volume can be based on the received one or more operating parameters, and in some embodiments, the volumetric image data itself. For example, one or more segmented features (e.g., an organ boundary, a vascular structure, or the like) can impact the virtual treatment volume in addition to the received operating parameters. In some cases, such segmented features can impact the thermal properties of the tissue proximate the segmented needle(s), and therefore impact the thermal effect of the needle on the proximate tissue.

The method of FIG. 16 further includes the step of updating the cross-sectional view of the volumetric image data (1610), for example, by rotating the volumetric image data about the needle axis (1612), and displaying the updated cross-sectional view (1604). Other processes can be used to update the cross-sectional view, such as selecting a different one of a plurality of needles for defining a needle axis, thereby adjusting the plane of the cross-sectional image to include the new needle axis.

Visualization techniques as described herein, including segmenting volumetric image data and rotating volumetric image data about a needle (e.g., real or virtual) axis can be useful in planning and/or performing an operation, such as a cryoablation process using one or more cryoneedles. In some examples, various techniques described herein can be performed in succession to assist in planning and performing a procedure.

Figure 17:
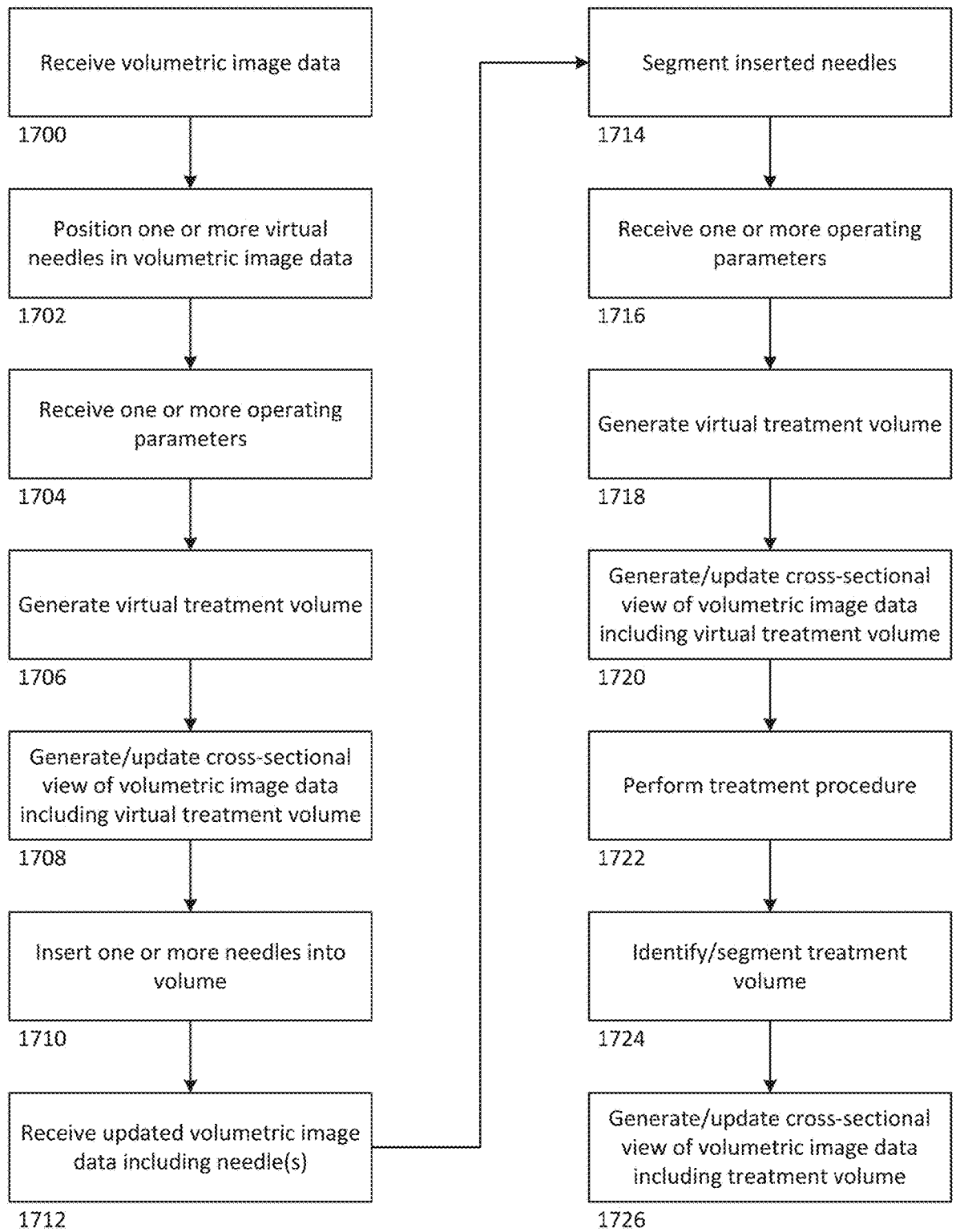
FIG. 17 is a process-flow diagram illustrating an exemplary process for planning and performing a procedure.

FIG. 17 is a process-flow diagram illustrating an exemplary process for planning and performing a procedure. The method includes receiving volumetric image data (1700), positioning one or more virtual needles in the volumetric image data (1702) and receiving one or more operating parameters (1704). The method further includes generating a virtual treatment volume (1706), which can be based, for example, on the location and number of the virtual needles and/or the received one or more operating parameters. As described elsewhere herein, a cross-sectional view of the volumetric image data including the virtual treatment volume can be generated/displayed (1708). Similarly, in the event the number of position of needles and/or the operating parameters are adjusted (e.g., via a user), the cross-sectional view can be updated.

In some implementations, the cross-sectional image including the virtual treatment volume can be used to plan a treatment procedure, with a system operator being able to view the treatment volume in combination with the volumetric image data. As described elsewhere herein, in some examples, various features (e.g., one or more lesions, organ boundaries, etc.) can be segmented the virtual treatment volume, and such segmented features and/or the virtual treatment region can be presented in a contrasting display scheme within the volumetric image data. The cross-sectional display can be used to facilitate analysis of the virtual needle location(s) and/or operating parameters used to generate the virtual treatment volume. Further, as discussed, the cross-sectional view can be rotated, for example, about the axis of a virtual needle, for example, in order to observe the relative location and size of the virtual treatment volume with respect to the volumetric image data, and in some instances, one or more segmented features therein.

The method of FIG. 17 further includes the step of inserting one or more needles into the volume (1710), for example, into tissue of a patient represented by the volumetric image data. In some cases, the one or more needles can be inserted in approximately the locations in the volume at which one or more virtual needles were positioned (e.g., at step 1702). A virtual treatment volume based on the location of the virtual needles can therefore provide a prediction of the outcome of a treatment performed by the inserted one or more actual needles.

The method further includes receiving updated volumetric image data that includes the one or more needles (1712), and segmenting the inserted needles in the updated volumetric image data (1714). In various embodiments, the virtual needles may be deleted from the volumetric image data, or may remain in the volumetric image data in combination with the segmented needles. In some such examples, the system may present the remaining virtual needles in a contrasting display scheme from the segmented needles in the volume.

In some examples, the method includes the steps of receiving one or more operating parameters (1716) and generating a virtual treatment volume (1718). In some embodiments, the one or more operating parameters in step 1716 are the same as those received in step 1704, and can be used in combination with the number and/or position of the inserted needles to generate a virtual treatment volume (1718). In some such examples, any differences between the generated treatment volume of step 1706 and the generated treatment volume of step 1718 is due to differences in the number and/or location of actual needles inserted in step 1710 from the number and/or location of virtual needles positioned in step 1702.

The method can include the step of generating/updating a cross-sectional view of volumetric image data that includes the virtual treatment volume (1720). In some such examples, the cross-sectional view of the volumetric image data includes one or more segmented inserted needles and/or additional segmented features from the volumetric image data. In some cases, such a cross-sectional view can be used to confirm the expected results of a procedure given the location of the needles inserted into the volume. Similarly, a user may view a virtual treatment volume that is based on the location of one or more inserted needles and determine that the position of the needle(s) should be adjusted in order to achieve a desired procedure outcome and/or to prevent an undesired treatment outcome. As described elsewhere herein, the cross-sectional view can be updated, for example, by rotating the volumetric image data about a needle axis defined by one or more of the inserted needles in order to view the cross-section of the virtual treatment volume in multiple planes.

If the virtual treatment volume is satisfactory, the method can include the steps of performing a treatment procedure (1722), such as a cryoablation, for example, identifying and/or segmenting a treatment volume (1724), and generating/updating a cross-sectional view of the volumetric image data including the treatment volume (1726). Thus, in an exemplary implementation, a user operating a surgical device, such as a cryoneedle, can observe the treatment volume in the volumetric image data, for example, to determine whether or not sufficient treatment is applied and/or whether or not treatment is progressing as expected (e.g., based on previously-viewed virtual treatment volumes).

As described with respect to the methods shown in FIGS. 11, 15, and 16, various steps in the method of FIG. 17 may be omitted or permuted, and/or various additional steps may be added. Additionally or alternatively, various steps in the method of FIG. 17 may be performed manually or automatically. For example, in some embodiments, a processing system (e.g., via a control system) may be configured to control operation of one or more surgical tools, such as ablation probes/needles, and may continue to perform a procedure (e.g., a cryo or other ablation procedure) until the treatment volume (e.g., an iceball, ablated tissue volume, tissue death volume an iceball or other respective margin, one or more isotherm regions, etc.) satisfies one or more conditions (e.g., sufficiently overlaps a segmented lesion, etc.).

In some examples, a system can be configured to additionally or alternatively automate the placement or movement of one or more needles (e.g., virtual needles) within the volume and/or to adjust one or more treatment (e.g., cryo or other ablation) parameters, such as in a treatment planning procedure. For example, in some embodiments, a system may be configured to determine an optimized location for one or more needles and/or one or more treatment parameters (e.g., ablation power, frequency, duration, etc.) for a simulated treatment. Optimized location and/or parameters may correspond to parameters that result in effective treatment while minimizing undesired outcomes, such as undesired tissue destruction.

As described elsewhere herein, several steps in a treatment simulation process (e.g., using virtual needles and/or real needles) and/or a treatment process (e.g., iceball formation via a cryoablation process) can be performed automatically by a system, for example, via processing system 90. While various steps are discussed with reference to a control system and a visualization system, it will be appreciated that, in various embodiment, such system steps may be performed by a single processor or distributed network of processors (e.g., via a processing system). That is, a visualization system and a control system need not be separate or distinguishable entities. On the other hand, in some examples, visualization system and control system can be embodied in separate, stand-alone components, such as separate computer workstations or the like. In some such embodiments, such systems may communicate with one another or with a common processing component, for example, for performing control processes (e.g., starting or stopping cryo or other ablation) in response to analyzed image data.

Further, while often described with respect to cryoablation, various processes described herein can be utilized in a variety of systems. For example, other tissue destruction processes (e.g., thermal ablation) can result in identifiable treatment volumes within volumetric image data, such as ablated tissue volumes or volumes of tissue within which tissue death is predicted to occur. Such treatment volumes may be segmented as described herein to facilitate visual analysis of treatment progress. Similarly, virtual treatment volumes may be generated as described herein to assist in treatment planning. In some cases, various processes as described herein can be used for other applications, such as ultrasound therapy or other process in which visualization from a plurality of orientations can be beneficial.

Additionally, visualization techniques as described herein (e.g., identifying a needle axis, taking a cross-section at a plane including the needle axis, rotating the cross-sectional view about the needle axis, etc.) can be used to visualize data from various perspectives. This can help ensure the sufficient treatment is performed (e.g., during a treatment process), that a prescribed treatment will likely be effective (e.g., during a treatment planning), and can reduce the risk for inadvertently damaging or otherwise negatively impacting undesired tissue (e.g., organs proximate a lesion).

Various examples have been described. The figures and descriptions herein are exemplary in nature and do not limit the scope of the invention in any way. Rather, such examples are provided to demonstrate various possible configurations and implementations within the scope of the following claim(s).

The invention claimed is:

1. A method for planning an ablation procedure prior to performing the procedure, the method comprising:
receiving volumetric image data representing a volume of patient tissue, the volumetric image data being constructed from a series of two-dimensional images of the patient tissue and including a virtual needle, each of the images in the series of two-dimensional images being generated by a visualization system that is configured to generate the series of two dimensional images based on an axis extending through the virtual needle and the volumetric image data representing the volume of patient tissue, wherein the virtual needle comprises a cryoneedle;
initiating a virtual cryoablation procedure by generating a virtual treatment volume about a feature of the patient tissue with the cryoneedle;
segmenting the virtual needle within the volumetric image data such that the virtual needle defines a longitudinal axis extending through the volume;
generating a first cross-sectional, two-dimensional view of the volume, the first cross-sectional, two-dimensional view showing a first plane through the volume in which the axis defined by the virtual needle lies;
displaying the first cross-sectional, two-dimensional view on a display; and
generating and displaying a second cross-sectional, two-dimensional view of the volume, the second cross-sectional, two-dimensional view showing a second plane through the volume in which the longitudinal axis defined by the virtual needle lies, the second plane being different from the first plane, intersecting the first plane at an angle so as to be noncoplanar with the first plane, and being coaxial with the first plane along the longitudinal axis of the virtual needle;
comparing a first dimension of the feature of the patient tissue to a first dimension of the virtual treatment volume in the first cross-sectional, two-dimensional view; and
comparing a second dimension of the feature of the patient tissue to a second dimension of the virtual treatment volume in the second cross-sectional, two-dimensional view.

2. The method of claim 1, wherein the first cross-sectional, two-dimensional view and the second cross-sectional, two-dimensional view comprise perspective views of the first and second planes, respectively.

3. The method of claim 1, wherein
the first cross-sectional, two-dimensional view comprises a plurality of pixels;
the second cross-sectional, two-dimensional view comprises a plurality of pixels; and
the pixels in the first cross-sectional, two-dimensional view that correspond to the virtual needle also correspond to the virtual needle in the second cross-sectional, two-dimensional view.

4. The method of claim 1, wherein generating the second cross-sectional, two-dimensional view comprises rotating the volumetric image data around the axis defined by the virtual needle, and wherein the rotating the volumetric image data around the axis is performed in response to a command received via a user interface.

5. The method of claim 1, further comprising the step of receiving a location of the virtual needle within the volume.

6. The method of claim 1, wherein the displayed first cross-sectional, two-dimensional view and/or the displayed second cross-sectional, two-dimensional view includes a displayed indication of the location of the virtual needle within the volume.

7. The method of claim 1, further comprising the step of segmenting a lesion from the volumetric image data.

8. The method of claim 7, wherein the first cross-sectional, two-dimensional view and/or the second cross-sectional, two-dimensional view comprises a cross-sectional outline of the lesion.

9. The method of claim 1, further comprising the steps of:
receiving one or more input parameters for an ablation procedure; and
determining a treatment volume based on the received one or more input parameters.

10. The method of claim 9, wherein the one or more input parameters comprises an ablation power and/or an ablation duration.

11. The method of claim 1, further comprising:
segmenting a lesion from the volumetric image data;
receiving one or more input parameters for an ablation procedure;
determining a treatment volume based on the received one or more input parameters; and
comparing the determined treatment volume to the lesion volume.

12. The method of claim 11, wherein the first cross-sectional, two-dimensional view and/or the second cross-sectional, two-dimensional view comprises a cross-sectional outline of the treatment volume and/or the lesion.

13. The method of claim 11, further comprising determining and displaying treatment margins associated with the treatment volume and the lesion volume.

14. The method of claim 1, further comprising:
adjusting the position of the virtual needle in the volume;
segmenting the virtual needle in the adjusted position; and
generating a third cross-sectional, two-dimensional view on the display showing a third plane through the volume in which the axis defined by the virtual needle Ur the adjusted position lies.

15. The method of claim 14, wherein adjusting the position of the virtual needle comprises advancing the needle along the axis defined by the needle such that the third plane is the same plane as shown in a previous cross-sectional, two-dimensional view.

16. The method of claim 1, wherein the virtual needle comprises a first virtual needle, and further comprising the steps of adding a second virtual needle to the volume and segmenting the second virtual needle such that the second virtual needle defies a longitudinal axis extending through the volume.

17. The method of claim 16, further comprising generating a fourth cross-sectional, two-dimensional view on the display showing a fourth plane through the volume in which the axis defined by the second virtual needle lies.

18. The method of claim 17, further comprising the step of receiving, via a user interface, a selection of which of the first and second virtual needle to include in a cross-sectional, two-dimensional view.

19. The method of claim 1, further comprising:
receiving a selection of a desired treatment volume;
determining a suggested needle position and/or one or more suggested ablation parameters to achieve the desired treatment volume; and
generating a fifth cross-sectional, two-dimensional view of the volume, the fifth cross-sectional, two-dimensional view showing a fifth plane through the volume in which the axis defied by the virtual needle in the suggested needle position lies.

20. The method of claim 1, further comprising: continuing the virtual cryosurgery procedure if the first dimension of the feature exceeds the first dimension of the virtual treatment volume and/or the second dimension of the feature exceeds the second dimension of the virtual treatment volume; and
indicating that formation of the virtual treatment volume is complete if the first dimension of the virtual treatment volume exceeds the first dimension of the feature and the second dimension of the virtual treatment volume exceeds the second dimension of the feature.

21. A method for planning an ablation procedure prior to performing the ablation procedure, the method comprising:
receiving volumetric image data including data representative of the location of a needle in the volume, the volumetric image data being constructed from a series of two-dimensional images of the patient tissue and including a virtual needle, each of the images in the series of two-dimensional images being generated by a visualization system that is configured to generate the series of two-dimensional images based on an axis extending through the virtual needle and the volumetric image data representing the volume of patient tissue, wherein the virtual needle comprises a cryoneedle;
initiating a virtual cryoablation procedure by generating a virtual treatment volume about a feature within the patient tissue with the cryodneedle;
segmenting the needle in the volumetric image data, the segmenting including determining a location of the needle in a volume;
generating and displaying a first cross-sectional, two-dimensional view of the volume, the first cross-sectional view showing a first plane through the volume in which the needle lies;
generating and displaying a second cross-sectional, two-dimensional view of the volume, the second cross-sectional view showing a second plane through the volume in which the needle lies, the second plane being different from the first plane, intersecting the first plane at an angle so as to be noncoplanar with the first plane, and being coaxial with the first plane along the longitudinal axis of the virtual needle;
comparing a first dimension of the feature of the patient tissue to a first dimension of the virtual treatment volume in the first cross-sectional, two-dimensional view; and
comparing a second dimension of the feature of the patient tissue to a second dimension of the virtual treatment volume in the second cross-sectional, two-dimensional view.

22. The method of claim 21, further comprising:
receiving one or more inputs related to an ablation procedure;
determining an impacted volume based on the one or more received inputs; and
displaying on the first cross-sectional, two-dimensional view and/or the second cross-sectional two-dimensional view a cross-sectional of the determined impacted volume.

23. The method of claim 22, wherein the received one or more inputs comprises an ablation power and/or art ablation time.

24. The method of claim 22, further comprising:
segmenting an identifiable volumetric region of interest in the volumetric image data; and
indicating the cross-sectional area of the identifiable volumetric region in the first cross-sectional two-dimensional view and/or the second cross-sectional, two-dimensional view.

25. The method of claim 24, further comprising the step of comparing the volume of the identifiable volumetric region of interest and the determined impacted volume.

26. The method of claim 25, wherein the comparing the volume of the identifiable volumetric region of interest and the determined impacted volume comprises comparing the boundaries of the volumetric regions, and wherein, if the boundary of the impacted region does not sufficiently enclose the identifiable volume of interest, adjusting a treatment variable.

27. The method of claim 26, wherein adjusting a treatment variable comprises adjusting a needle position, adjusting an ablation power, adjusting an ablation time, and/or adding one or more additional needles into the volume.

28. The method of claim 21, further comprising: continuing the virtual cryosurgery procedure if the first dimension of the feature exceeds the first dimension of the virtual treatment volume and/or the second dimension of the feature exceeds the second dimension of the virtual treatment volume; and indicating that formation of the virtual treatment volume is complete if the first dimension of the virtual treatment volume exceeds the first dimension of the feature and the second dimension of the virtual treatment volume exceeds the second dimension of the feature.

\* \* \* \* \*